(12) United States Patent
Phanstiel

(10) Patent No.: US 7,001,925 B1
(45) Date of Patent: Feb. 21, 2006

(54) COMPOUNDS AND METHOD FOR ENHANCING THE EFFICACY OF ANTI-CANCER DRUGS

(75) Inventor: Otto Phanstiel, Oviedo, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 36 days.

(21) Appl. No.: 10/667,288

(22) Filed: Sep. 19, 2003

Related U.S. Application Data

(60) Provisional application No. 60/414,037, filed on Sep. 27, 2002.

(51) Int. Cl.
*A61K 31/13* (2006.01)

(52) U.S. Cl. .................. 514/654; 564/367; 564/368

(58) Field of Classification Search ............... 564/367, 564/368; 514/654
See application file for complete search history.

(56) References Cited

U.S. PATENT DOCUMENTS

| | | | | |
|---|---|---|---|---|
| 5,109,024 | A | 4/1992 | Prakash et al. | 514/674 |
| 5,719,193 | A | 2/1998 | Bowlin et al. | 514/673 |
| 5,866,613 | A | 2/1999 | Bergeron | 514/674 |
| 6,235,794 | B1 * | 5/2001 | Bergeron, Jr. | 514/674 |
| 6,281,371 | B1 | 8/2001 | Klosel et al. | 554/51 |
| 6,319,956 | B1 | 11/2001 | Iwata | 514/674 |
| 6,342,534 | B1 | 1/2002 | Bergeron | 514/673 |
| 2002/0067472 | A1 | 6/2002 | Iwata | 353/122 |

OTHER PUBLICATIONS

Bair et al. Chem. Abst. 113:114786 (1990).*
Aug. 1, 1992, Holley, et al., Targeting of Tumor Cells and DNA by a Chlorambucil-Spermidine Conjugate, pp. 4190-4195.
1995, Cullis, et al, Conjugation of a Polyanime to the Bifunctional Alkylating Agent Chlorambucil Does Not Alter the Preferred Cross-Linking Site in Duplex DNA, pp. 8033-8034.
1997, Bergeron, et al., A Comparison of Structure-Activity Relationships between Spermidine and Spermine Analogue Antineoplastics, pp. 1475-1494.
Aug. 16, 2000, Phanstiel, et al., The Effect of Polyamine Homologation on the Transport and Cytotoxicity Properties of Polyamine—(DNA-Intercalator) Conjugates, pp. 5590-5599A-J.
Sep. 28, 2001, Wang, et al., Influence of Polyamine Architecture on the Transport and Topoisomerase II Inhibitory Properties of Polyamine DNA-Intercalator Conjugates, pp. 3682-3691.
Oct. 2, 2002, Delcros et al, Effect of Spermine Conjugation on the Cytotoxicity and Cellular Transport of Acridine, pp. 5098-5111.

* cited by examiner

*Primary Examiner*—Peter O'Sullivan
(74) *Attorney, Agent, or Firm*—Brian S. Steinberger; Law Offices of Brian S. Steinberger, P.A.

(57) ABSTRACT

Polyamine compounds, method of synthesis and method of use for anti-cancer purposes, and for enhancing the activity of existing anti-cancer drugs are provided. This disclosure has identified certain polyamine motifs that can be attached to toxic agents to facilitate their access to cancer cells as well as polyamine compounds of surprising cytotoxicity and selectivity in killing cancer cells. It includes an illustrative conjugate system with examples of a triamine or a tetraamine appended to a cytotoxic agent. There are five method schemes illustrative of the synthesis of the compounds of the invention. Included is a general strategy to enhance cell uptake by attaching a polyamine vectoring system with an example of a triamine vector attached to an existing anti-cancer drug to improve its chemotherapeutic potency. There is an illustration of using the triamine vector to improve the selectivity of an anthracenylmethyl amine cytotoxic agent (e.g. an anthracenylmethyl-4,4-triamine conjugate outperformed an anthracenylmethyl N-butyl amine derivative). There is an illustration of a synthetic method to attach the polyamine vector onto an existing chemotherapeutic, doxorubicin. This methodology can lead to the synthesis of the polyamine-doxorubicin conjugate. There are illustrations of the synthesis of various alkyl aryl substituted polyamines, a hydroxylated polyamine derivative and a cyclohexyldiamine analogue.

17 Claims, 11 Drawing Sheets

Schem 3

14

15

Conjugates

14: q=2,r=2: Doxo-triamine
15: q=2,r=2, s=2:Doxo-tetraamine

COMPOUNDS AND METHOD FOR ENHANCING THE EFFICACY OF ANTI-CANCER DRUGS

This invention claims the benefit of priority based on U.S. Provisional Patent Application Ser. No. 60/414,037 filed Sep. 27, 2002 and was supported in part by Elsa U. Pardee Foundation grant #11–64-882, 11–66-807, a Research Corporation grant #11–64-872, University of Central Florida Sponsored Research grant #11–64-938, University of Central Florida—Center for Discovery of Drugs and Diagnostics ($CD^3$) grant #20–04-005, and the Florida Hospital Gala Endowed Program for Oncologic Research grants #11–64-874, 11–64-879, 11–64-883, 11–64-892, 11–66-809.

FIELD OF INVENTION

This invention relates to polyamine compounds and more particularly to their use as anticancer agents and their use as a vector for the enhancement of anti-cancer drug activity.

BACKGROUND AND PRIOR ART

One of the major shortcomings of current cancer therapies is the non-selective delivery of the antineoplastic drug to both targeted tumor cells and healthy cells. Enhanced selectivity of such drugs could diminish their associated toxicity by reducing their uptake by healthy cells. Moreover, selective delivery would increase drug potency by lowering the effective dosage required to kill the affected cell type. Vectored systems, which have enhanced affinity for cancer cells would be an important advance in cancer therapy.

Polyamines are naturally occurring amines, which form polycations in vivo. These stabilize DNA architectures and are cellular growth factors. All cells contain some form of the native polyamines: putrescine, spermidine or spermine. Rapidly dividing cells (such as cancer cells) require large amounts of polyamines, and cells can either biosynthesize or import these essential growth factors. Many tumor cell lines have been shown to have very high levels of polyamines and an active polyamine transporter.

Polyamine structures have been exploited for use in various drug strategies, such as demonstrated in United States Patents: Bergeron, U.S. Pat. Nos. 6,342,534 and 5,866,613; Prakash, U.S. Pat. No. 5,109,024; Iwata U.S. Pat. No. 6,319,956 and Published application 2002/0067472 A1; Bowlin U.S. Pat. No. 5,719,193; and, Klosel U.S. Pat. No. 6,281,371 B1 and published document "A Comparison of Structure-Activity Relationships between Spermidine and Spermine Analogue Antineoplastics," by Bergeron, R. J.; Feng, Y.; Weimar, W. R.; McManis, J. S.; Dimova, H.; Porter, C.; Raisler, B.; Phanstiel IV, O. *J. Med. Chem.* 1997, 40, No. 10, 1475–1494.

Bergeron U.S. Pat. No. 6,342,534 should be considered with respect to Column 3, lines 51–67 and Column 4, lines 39–48, Table 1 and Table 2, in which the emphasis is on bis-substituted tetraamine systems terminated with N-ethyl, N-piperidinyl, and pyridinyl units. Bowlin referred to above should be considered with respect to Column 1, lines 51–67 in which is described, compounds useful for potentiating the immune response. Bowlin's compounds are limited to activating cells to be killed by the immune system. Thus, Bowlin requires an immune system to work with their disclosed drugs.

Other research in using polyamine conjugates for cellular entry has been described in published documents (Cohen, G. M.; Cullis, P.; Hartley, J. A.; Mather, A. Symons, M. C. R.; Wheelhouse, R. T. Targeting of Cytotoxic Agents by Polyamines: Synthesis of a Chloroambucil-Spermidine Conjugate. *J. Chem. Soc. Chem. Commun.* 1992, 298–300; Cullis, P. M.; Merson-Davies, L.; Weaver, R. Conjugation of a polyamine to the bifunctional alkylating agent chlorambucil does not alter the preferred crosslinking site in duplex DNA. *J. Am. Chem. Soc.* 1995, 117, 8033–8034; Phanstiel IV, O.; Price, H. L,; Wang, L.; Juusola, J.; Kline, M.; Shah, S. M. The Effect of Polyamine Homologation on the Transport and Cytotoxicity Properties of Polyamine-(DNA-Intercalator) Conjugates. *J. Org. Chem.* 2000, 65, 5590–5599; Wang, L.; Price, H. L.; Juusola, J.; Kline, M.; Phanstiel, IV, 0. "Influence of Polyamine Architecture on the Transport and Topoisomerase II Inhibitory Properties of Polyamine DNA-Intercalator Conjugates," *J. Med. Chem.* 2001, 44, 3682–3691; Delcros, J-G.; Tomasi, S.; Carrington, S.; Martin, B.; Renault, J.; Blagbrough, I. S.; Uriac, P. Effect of spermine conjugation on the cytotoxicity and cellular transport of acridine. *J. Med. Chem.,* 2002, 45, 5098–5111).

The prior art by Cullis et al is limited to delivering a DNA-alkylating agent (chlorambucil) to cells using spermidine, a non-optimal polyamine vector. The chlorambucil substituent is linked via a tether to the internal $N^4$-nitrogen of the spermidine chain. Recent findings have shown this internal N-alkylation motif used by Cullis to be a less than optimal arrangement for using the polyamine transporter. The previous publications by Phanstiel IV et al are limited to branched polyamine systems built from spermine and spermidine platforms, again using non-optimized polyamine vectors. The report by Blagbrough et al focused on using tetraamine derivatives of spermine to deliver acridine to cells. Blagbrough's compounds are limited by the use of less than optimal spermine vectors to deliver a less potent acridine drug into cells.

Since the 1980s several laboratories have probed the transport properties of polyamines into various cell types (*E. coli*, yeast and mammals). The polyamine transporter in *E. coli* is perhaps the best understood as the transporter gene and several protein gene products (Pot A–F) have been identified. In particular the PotB and PotC proteins form a trans-membrane channel, which facilitates polyamine transport. PotD is a periplasmic, polyamine-binding protein, which prefers spermidine over putrescine. Moreover, the X-ray crystal structure of spermidine bound to PotD revealed that the molecular recognition events involved in spermidine binding is controlled by specific amino acid residues and a bound water molecule. Specifically, through this water molecule, the bound spermidine molecule forms two hydrogen bonds with Thr 35 and Ser 211. In a related study the PotF protein was shown to selectively bind putrescine. The PotF crystal structure, in combination with the mutational analysis, revealed the residues crucial for putrescine binding (Trp-37, Ser-85, Glu-185, Trp-244, Asp-247, and Asp-278) and the importance of water molecules for putrescine recognition. Therefore, the *E. coli* studies provided a striking example of how cells can discriminate between structurally similar di-and tri-amine substrates, (e.g., putrescine (PUT) and spermidine (SPD), respectively). While significant work has also been accomplished in yeast and other systems, the proteins involved in mammalian polyamine transport have not yet been isolated and characterized beyond a kinetic description. Clearly, the lack of structural detail associated with the mammalian polyamine transporter is a glaring void in the knowledge base.

SUMMARY OF THE INVENTION

The first objective of the present invention is to provide compounds that are useful as anti-cancer agents.

The second objective of the present invention is to provide a method for enhancing the efficacy of anti-cancer agents.

The third objective of the present invention is to provide a method for preparing the anti-cancer compounds.

The fourth objective of the present invention is to provide compounds and methods for treating cancer cells without requiring the immune system.

Preferred embodiments of this invention include:

Compounds of Formula A,

A:

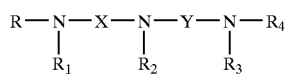

or a pharmaceutically acceptable salt thereof, wherein R is selected from the group consisting of naphthylmethyl, naphthylethyl, anthracenylmethyl, anthracenylethyl, pyrenylmethyl, $R^1$, $R^2$, $R^3$, $R^4$ are selected from at least one of hydrogen, alkyl, cycloalkyl, alkylaryl, para-toluenesulfonyl, arenesulfonyl, alkylsulfonyl, acyl, carbamoyl, where X is at least one of cycloalkyl and $(CH_2)_r$, and r is 2–18 and Y is at least one of cycloalkyl and $(CH_2)_s$ and s is 2–18.

Compounds of the Formula B,

B: $RNR'(CH_2)_rNR^2(CH_2)_sNR^3(CH_2)_tNR^4R^5$ or a pharmaceutically acceptable salt thereof, wherein R is selected from the group consisting of naphthylmethyl, naphthylethyl, anthracenylmethyl, anthracenylethyl, pyrenylmethyl, wherein $R^1$, $R^2$, $R^3$, $R^4$ and $R^5$ are selected from at least one of the following: hydrogen, alkyl, cycloalkyl, alkylaryl, para-toluenesulfonyl, arenesulfonyl, alkylsulfonyl, acyl, carbamoyl and r is 2–18, s is 2–18 and t is 2–18;

Compounds of the Formula C,

C: $RNR'(CH_2)_rNR^2(CH_2)_sNR^3R^4$ or a pharmaceutically acceptable salt thereof, where R is a chemotherapeutic agent and $R^1$–$R^4$ are at least one of hydrogen, alkyl, acyl, carbamoyl or alkylaryl, and r is 2–18, and s is 2–18;

A Compound of the Formula D,

D: $RNR'(CH_2)_rNR^2(CH_2)_sNR^3(CH_2)_tNR^4R^5$ or a pharmaceutically acceptable salt thereof, where R is a chemotherapeutic agent and $R^1$–$R^5$ are at least one of hydrogen, alkyl, acyl, carbamoyl or alkylaryl, and r is 2–18, s is 2–18 and t is 2–18; their use in pharmaceutical compositions; and their methods of fabrication.

Further objects and advantages of this invention will be apparent from the following detailed descriptions of the presently preferred embodiments, which are illustrated schematically in the accompanying drawings.

DESCRIPTION OF THE PREFERRED EMBODIMENTS

Figure 1:
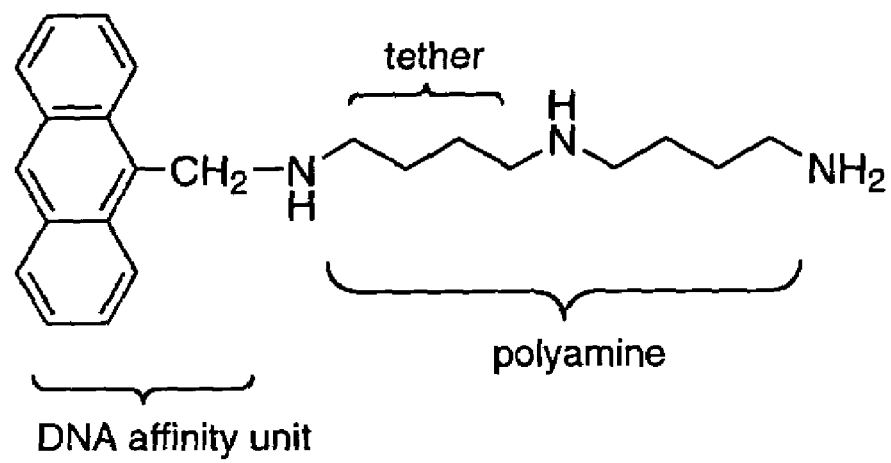
FIG. 1 is a sample conjugate system with two examples, triamine 8 and tetraamine 13.
Figure 1:
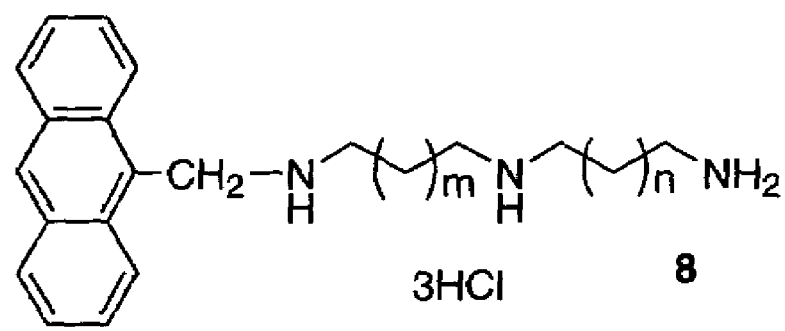
Figure 1:
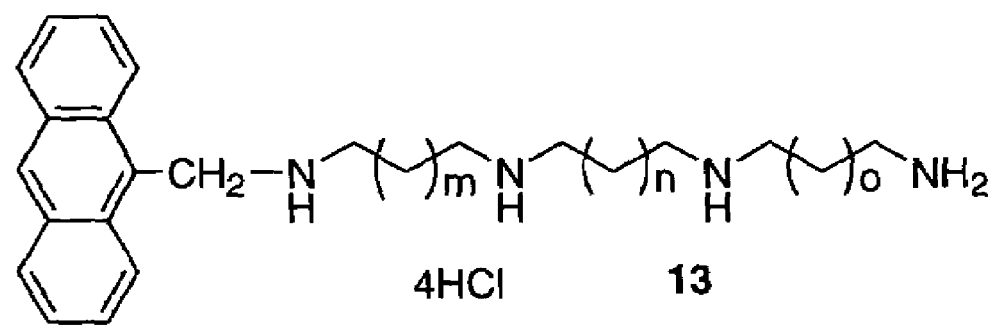

Before explaining the disclosed embodiments of the present invention in detail it is to be understood that the invention is not limited in its application to the details of the particular arrangements shown, since the invention is capable of other embodiments. Also, the terminology used herein is for the purpose of description and not of limitation.

It would be useful to discuss the definitions of some words used herein and their applications before discussing the invention, which provides compounds and methods for treating cancer cells without requiring the immune system for their cytotoxicity. For the purposes of this patent application, the term "vector" is used to denote a special chemical message, which is recognized by the polyamine transport system of cells. This special chemical message is a polyamine with the proper or ideal spacing units in between the nitrogen centers. Research has shown that having the proper spacing unit (distance between the nitrogen centers) and having the appropriate number of positive charges (via protonation of the nitrogen centers) is critical for selective cellular uptake.

1) "Vectored systems" relates to polyamine conjugates, which have a polyamine message which is recognized by the polyamine transport system on the surface of cells and have enhanced uptake into cells with highly active polyamine transporters over those which do not, (e.g., CHO vs. CHO-MG cells).

2) The term "transporter" is used to describe the cellular process of binding and/or importing a chemical entity, which is outside the cell. The chemical entity in this case is the polyamine conjugate, i.e. a polyamine scaffold covalently attached to a toxic agent.

3) The term "conjugate" is used to describe a polyamine architecture, which is covalently bound to a cytotoxic agent (e.g., an anthracenyl methyl unit) or to a known chemical agent with anti-cancer properties, e.g., doxorubicin.

4) "Cell selectivity" denotes the ability of a polyamine conjugate to selectively enter cells with highly active polyamine transporters (e.g. CHO cells or B 16 melanoma cells) over those that have lower polyamine transport activity (e.g. CHO-MG cells or Mel-A cells).

5) "IC$_{50}$ value" is the concentration of drug needed to kill 50% of the treated cell population. The lower the value the more cytotoxic the drug is to that cell type.

6) "K$_i$ value" reflects the affinity of the drug architecture for the polyamine transporter. The lower the value of the Ki the higher the affinity of the drug for the polyamine transporter.

7) L1210 cells are mouse leukemia cells and are a standard well-used benchmark for evaluating cytotoxicity of new drug systems, especially polyamine containing drugs.

8) Chinese hamster ovary cells (CHO cells) have an active polyamine transporter. This cell type is very susceptible to drugs, which use the polyamine transporter to gain access to cells (i.e. polyamine conjugates).

9) Chinese hamster ovary cells, which are chemically mutated to be polyamine transport-deficient will be referred to as the CHO-MG cell line.

This cell type should have lower susceptibility to polyamine conjugates, which use the polyamine transporter to gain access to cells, since it does not have an active transporter to facilitate their uptake.

10) B 16 cells are melanoma, skin cancer cells with highly active polyamine transporters. These cells should be very susceptible to polyamine conjugates which use the polyamine transporter to gain access to cells.

11) Mel-A cells are normal melanocytes, skin cells, which have moderately active polyamine transporters. These cells should be moderately susceptible to polyamine-conjugates, but less so than the B-16 cells.

This invention has identified polyamine compounds, which have surprising cytotoxicity, unexpected selectivity in killing cancer cells (or cells with active polyamine transporters), and/or facilitate the delivery of known toxic agents into cancer cells.

A panel of amine substrates of the general formula indicated in FIG. 1 (i.e., those of general type 8 and 13 as well as other systems to be discussed later) were tested for efficacy in cells containing active and deficient polyamine transporters (i.e., Chinese hamster ovary CHO cells and CHO-MG cells, respectively). In addition, murine leukemia (L1210) cells and L1210 cells pretreated with DFMO (Difluoromethylornithine, an inhibitor of ornithine decarboxylase) were also treated with the polyamines illustrated in FIG. 1 (i.e. those of general type 8 and 13) as well as other systems to be discussed later. The results indicate micromolar concentration IC$_{50}$ values in three cell lines along with varying K$_i$ values (a transporter affinity measure) and are provided in Tables 1 and 2. Table 1 illustrates the fact that different polyamine compounds have different cytotoxicity profiles, e.g., the IC$_{50}$ value varies from 0.3 to 36.3 uM in the L1210 cell study (Table 1, column 2). The presence of DFMO is known to enhance polyamine uptake into L1210 cells and should make the cells more sensitive to the tested polyamine analogues. Indeed, the IC$_{50}$ values were typically lower in the presence of DFMO (Table 1, column 3). This finding is consistent with certain analogues using the polyamine transporter to gain access to these cells. The distance separating the nitrogen centers was directly related to cytotoxicity. Attaching the anthracenylmethyl subunit to a particular polyamine "vector" motif provided enhanced cytotoxicity. The structures of compounds 8b–8g are defined in FIG. 2, Scheme 2. Note: the term "3,3-triamine" refers to the fact that molecule 8b has two three carbon spacer units separating the three nitrogen centers.

For example in Table 1, 8b, a conjugate bearing the "3,3-triamine" motif was only 1.3 fold more toxic in the presence of DFMO, whereas the related 4,4-triamine motif 8e was twice as toxic. This effect was even more dramatic with tetraamine systems 13e and 13f, which were 7.2 and 4.7 fold more toxic, respectively, in the presence of DFMO. Note the control compounds 34 and 35, which do not contain the proper polyamine vector, gave lower cytotoxicity in the presence of DFMO (both were 0.7 fold less toxic). These results suggested that the observed cytotoxicity enhancement with DFMO is related to the ability of the conjugate to utilize the polyamine transport system.

As shown in Table 2, these same controls 34 and 35 were not very selective in killing CHO and CHO-MG cells as they had similar toxicities in both lines. Indeed, specific structures of the polyamine component were needed for the desired cell selectivity. The triamines of the invention have demonstrated over 150-fold higher cytotoxicity in killing cells with active polyamine-transporters (as modeled by the CHO line) over cells, which are polyamine-transporter deficient (as modeled by the CHO-MG cell line). For example, the 4,4-triamine conjugate 8e was one of the most selective compounds and was very toxic to CHO cells (IC$_{50}$=0.45 μM), but much less so to the CHO-MG cell line (IC$_{50}$=66.7 μM).

While a few investigators have successfully "ferried" polyamine-drug conjugates into cells, limited systematic studies have been conducted on the mono-substituted linear polyamines as vector systems. This, in part, may stem from their less direct syntheses, which involve several steps. The method of synthesis of some of the triamines (and tetraamines) of the invention are provided in examples below and in FIGS. 2A, 2B, 2C, 5 and 6 (Schemes 1–7).

The initial conjugates are comprised of an anthracene nucleus covalently bound to a polyamine framework. The anthracene component was selected due to significant preliminary data, which revealed its increased potency over an acridine analogue in murine leukemia (L1210) cells. Moreover, the anthracene provides a convenient UV "probe" for compound isolation (and identification) and elicits a toxic response from cells upon entry (presumably through DNA coordination). The uptake of several anthracene-polyamine conjugates by the polyamine transporter (PAT) has been demonstrated. The large size and sweep volume of the appended anthracene system suggests that other architectures (e.g., doxorubicin) may also be conveyed into cells via this transporter. In fact, compound 27d, a pyrene derivative, is also selectively imported into cells with active polyamine transporters. Therefore, while the anthracene component offers a convenient probe for polyamine delivery studies, the invention is not limited thereto.

To optimize delivery, polyamine architectures are needed, which facilitate uptake via the polyamine transporter (PAT). The polyamine tail has been shown to facilitate uptake, impart water solubility to the conjugate, and enable dosing as aqueous solutions.

Virtually all cells contain substantial amounts of at least one of the polyamines: putrescine (PUT), spermidine (SPD), or spermine (SPM). Since the polyamine component represents an important cellular "feedstock", one would expect preferential uptake by rapidly dividing cells. Polyamines are a requirement for the optimum growth and replication of various cell types and are present in higher concentrations in rapidly proliferating cells. The fact that polyamines can be taken up by tissues from the circulation is known, since the metabolism of labeled polyamines has been studied rapidly dividing cells) take up exogenous polyamines in increased amounts via a specific transport system. The high specific activity of polyamine transport in tumor cells is thought to be associated with the inability of biosynthetic enzymes to provide sufficient levels of polyamines to sustain the rapid cell division. These "bio-production" constraints are partially offset by scavenging polyamines from exogenous sources.

Figure 3:
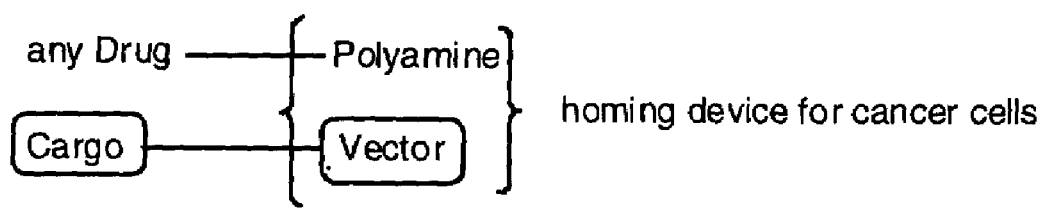
FIG. 3 is a general strategy to enhance cell uptake by polyamine vectoring systems.
Figure 4:
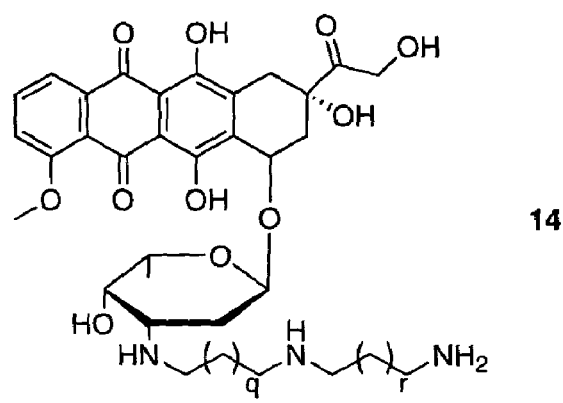
FIG. 4 provides examples of an existing anti-cancer drug doxorubicin substituted with either a triamine, e.g., 14 (or a tetraamine, e.g., 15) to improve its chemotherapeutic potency.
Figure 4:
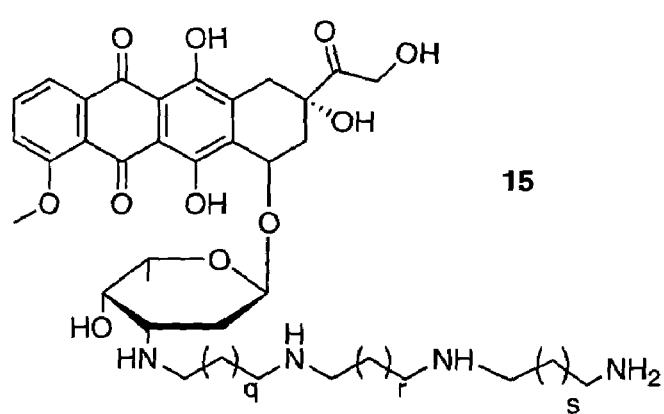

Additional studies have indicated that polyammonium cations (PACs) have a very high DNA affinity, but are loosely bound and can "read" DNA very rapidly because of their otherwise unconstrained motion. These properties make PACs and related polycations ideal for drug delivery when the drug needs to reach specific sites in the DNA. In short, polyamine-containing conjugates can act as recognition elements for the polyamine uptake apparatus and may also enhance DNA targeting via their electrostatic PAC-DNA interactions. These properties lay the foundation for a "value-added" vectoring system as indicated in FIG. 3. In addition to the demonstrated compounds, by attaching a polyamine architecture (as example, the 4,4 triamine) onto a current drug scaffold (e.g., doxorubicin), the potency and selectivity of the drug may be increased (14, FIG. 4). Alternatively, a tetraamine scaffold could also provide enhanced abilities, (15, FIG. 4).

This invention identifies efficient polyamine vector architectures required to harness the polyamine transporter. This, in turn, led to new drugs and drug delivery systems, which target rapidly dividing cancer cells over normal resting cells (e.g., melanoma cells over melanocytes, see Table 3). This is a discovery of significant therapeutic value in the fight against cancer. Moreover, this strategy has identified targeted antineoplastic agents, which are non-antibody based, as well as structural elements, which can be attached to other drugs to assist their entry into cells expressing a polyamine transporter.

The following examples are provided for the purpose of illustration and not limitation.

EXAMPLES

Figure 2A:
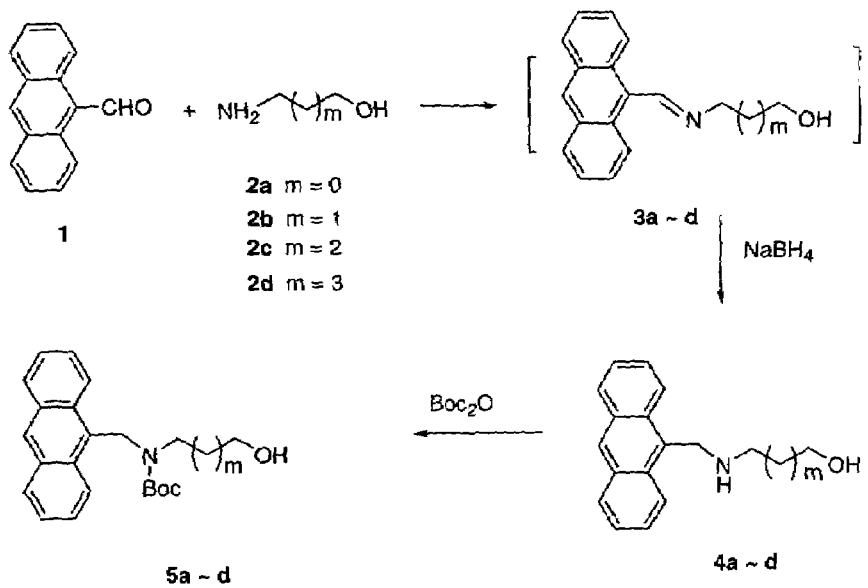
FIGS. 2A, 2B and 2C (Schemes 1–4) provide general method schemes for the synthesis of the compounds of the invention.
Figure 2A:
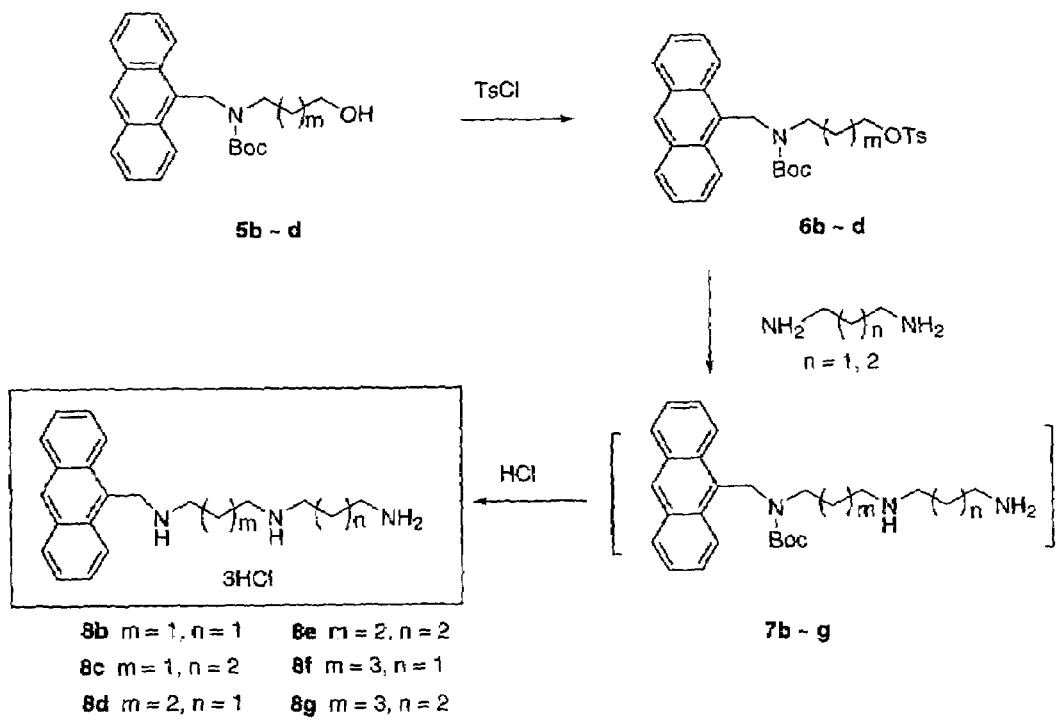

Synthesis: As shown in FIG. 2A, Scheme 1, the reductive amination of 1 to 4 was achieved in two steps via in situ generation of the imine 3. A homologous series of imines (3a–d) were prepared from 1 and different alcohols. Each imine was then reduced to its respective amine 4 with $NaBH_4$ in good yield without purification. Solvent removal by rotary evaporation at 40–50° C. facilitated imine formation and provided satisfactory yields of the 2° amines, 4a–d, (68–81%) after the two-step process. The 2° amines 4a–d were N-protected to form 5 using excess di-t-butyl dicarbonate, $Boc_2O$. Interestingly, compound 5b, which contained three methylene units, was unstable, even when it was stored at low temperature (0–5° C.) under nitrogen. This finding is in direct contrast to 5a, 5c and 5d, which were stable at room temperature.

In the seemingly routine tosylation step, shown in Scheme 2, we were unable to obtain the desired compound 6a from the N-Boc protected 5a. In addition, the impurities generated during the formation of 5b greatly affected the tosylation reaction. Nevertheless, tosylate 6b was isolated in lower yield (51%), but was unstable to prolonged storage. In contrast, tosylates 6c and 6d were prepared in higher yields (88%) and were relatively stable. However, their respective colors and $^1H$ NMR spectra slowly changed during prolonged storage in the refrigerator. Therefore, the tosylates 6 were best generated and used as soon as possible. Alternatively, methanesulfonyl chloride (i.e., mesyl chloride) can be used in lieu of tosyl chloride to activate the alcohol subunit. The advantage to using mesyl chloride is that it is readily removed by a 1N NaOH washing step. The yields using either sulfonylchloride agent are comparable. However, the isolation of synthetic intermediates, where OTs=O-mesyl instead of O-tosyl in Schemes 2–4 and Scheme 6, is more efficient and conducive to scale-up processes.

As shown in Scheme 2, the tosylated compounds (6b–d) were reacted with excess putrescine or 1,3-diaminopropane to form six N-Boc protected triamines 7b–g. These triamines could be cleanly isolated, but were again unstable to prolonged storage at low temperature. Therefore, they were consumed in the next step immediately after purification. The N-Boc groups of 7 were removed by 4N HCl, and the six triamine compounds 8b–g were formed in good yield. Impurities in 8 were removed by washing the solids with absolute ethanol.

After repeated syntheses, it was found that 5 and 6 could be used directly in subsequent steps to provide satisfactory yields and purities of the target compounds 8. Therefore, as long as adducts 4 and 7 were pure, one could avoid column chromatography on the other intermediates, 5 and 6.

As shown in Scheme 3, derivatives 4a–d were previously converted to their respective N,O-bis-tosylates 9a–d. Displacement of the terminal tosylate by butanediamine provided the series, 10a–d in good yield. Derivatives 10a–d represent triamine systems containing two large aromatic motifs and has one of the terminal amines sequestered as a sulfonamide.

Figure 2B:
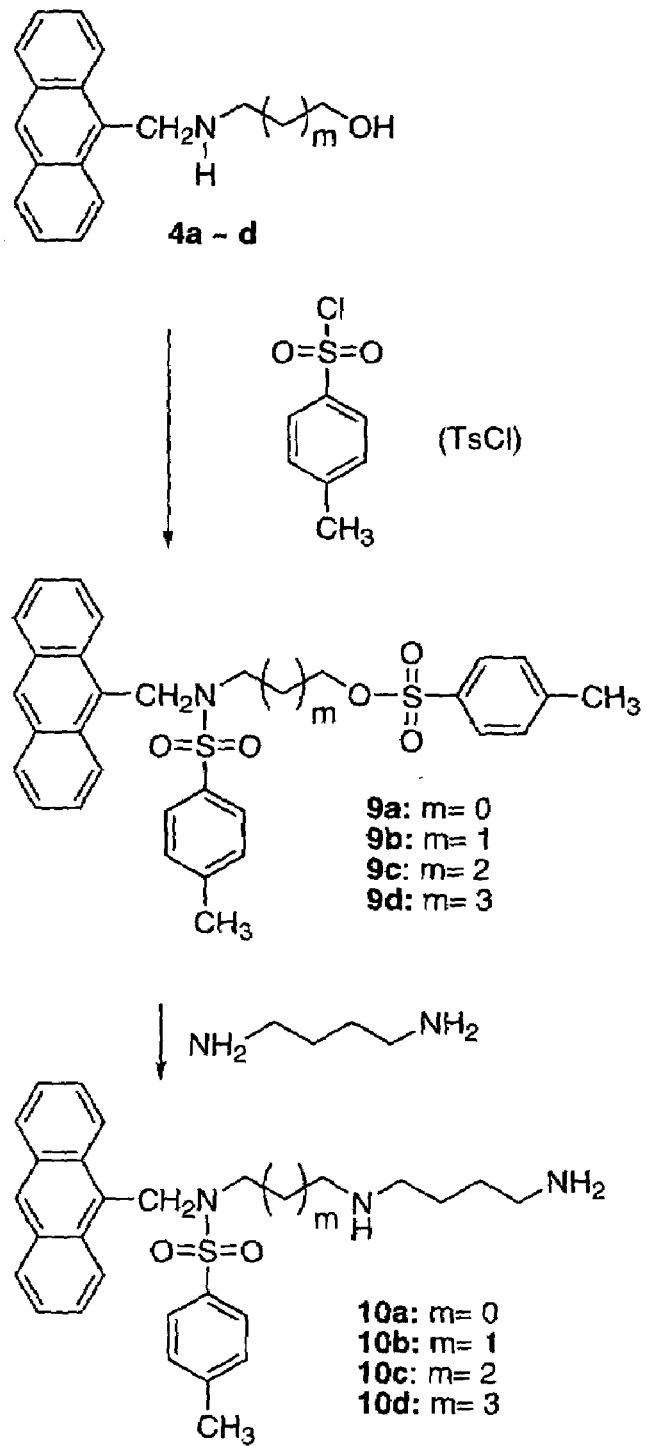
Figure 2C:
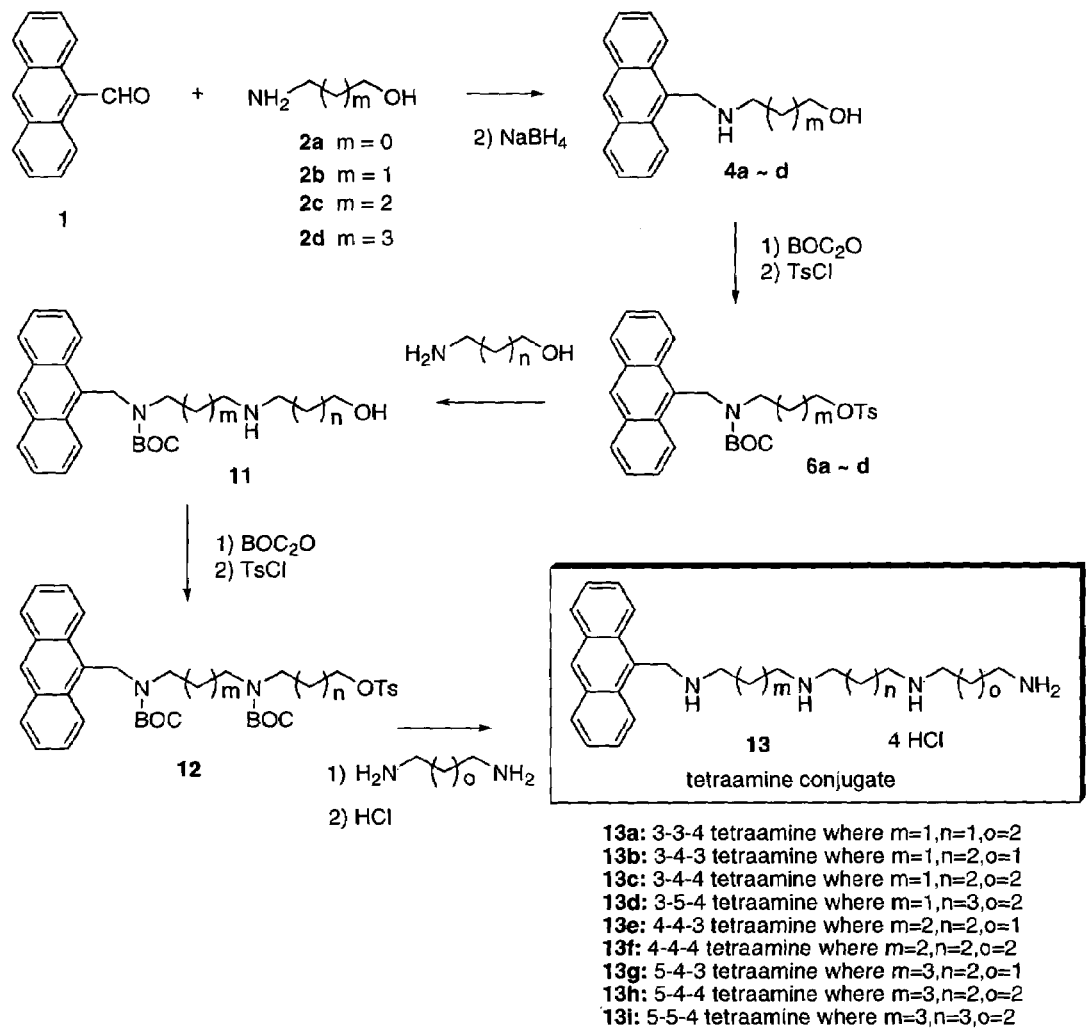

As shown in Scheme 4, tetraamine derivatives 13a–i were synthesized via intermediates 6, 11, and 12 using similar methods as shown for 8b–g in Schemes 1 and 2 (FIGS. 2A–2B). How these structural perturbations influence the cytotoxicity of the bioconjugate were evaluated via $IC_{50}$ and $K_i$ determinations are listed in Tables 1 & 2.

Figure 5:
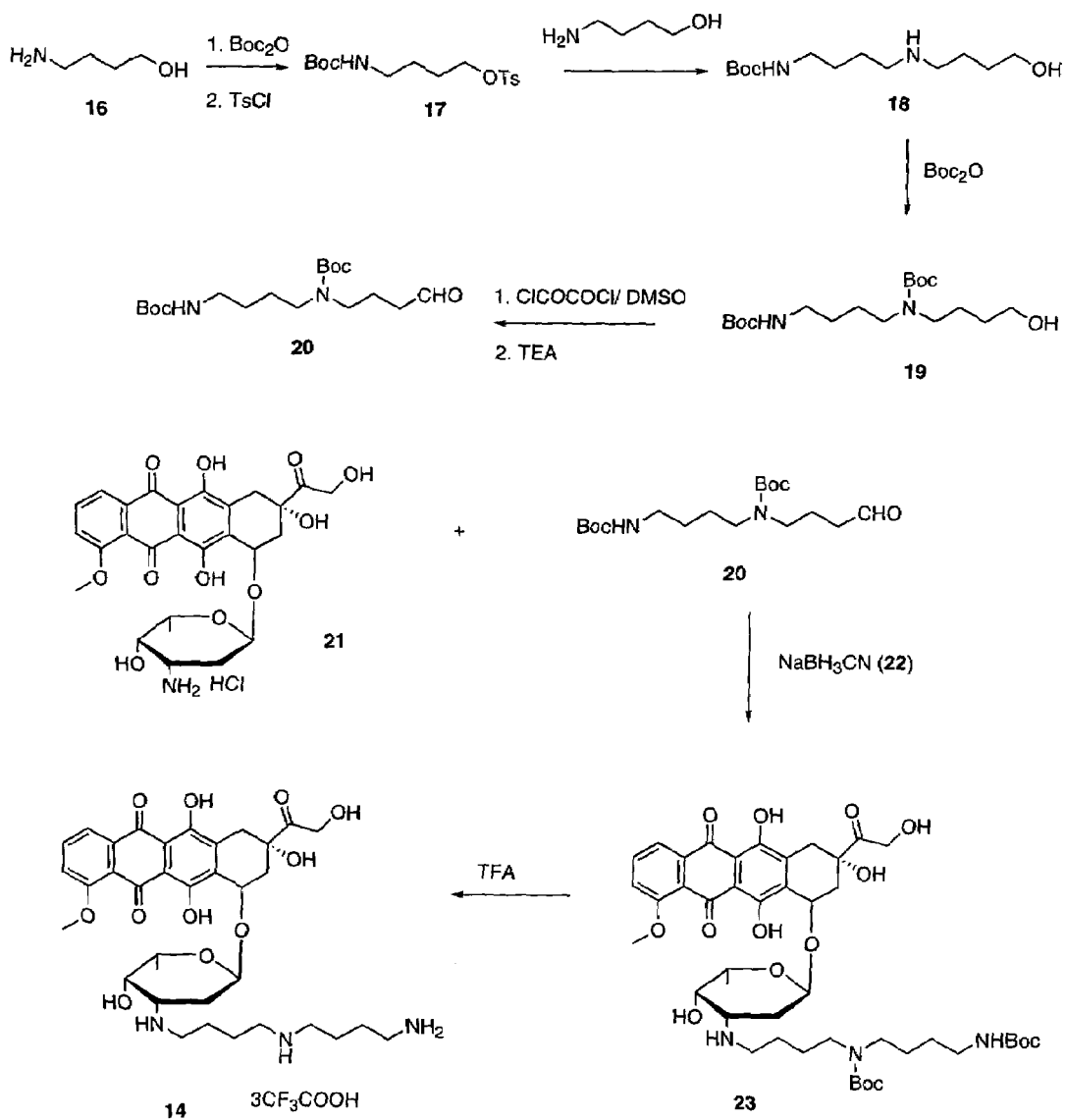
FIG. 5 (Scheme 5)—illustrates a synthetic method to attach the polyamine vector onto an existing chemotherapeutic, doxorubicin. This methodology can lead to the synthesis of the polyamine-doxorubicin conjugate 14.

FIG. 5 (Scheme 5) provides an example of a synthetic method to attach the polyamine vector onto an existing chemotherapeutic agent such as doxorubicin, 21. The use of an antineoplastic agent conjugated to the appropriate polyamine should provide enhanced antineoplastic activity. The synthetic methodology led to the synthesis of the N-Boc protected polyamine-doxorubicin conjugate 23 from which one obtains the doxorubicin-4,4-traimine conjugate, 14. Coupling an appropriate polyamine to other existing chemotherapeutic agents (e.g., mitoxantrone, anthramycin, camptothecin, vincristine or cis platin) should also provide an enhanced chemotherapeutic agent.

Figure 6A:
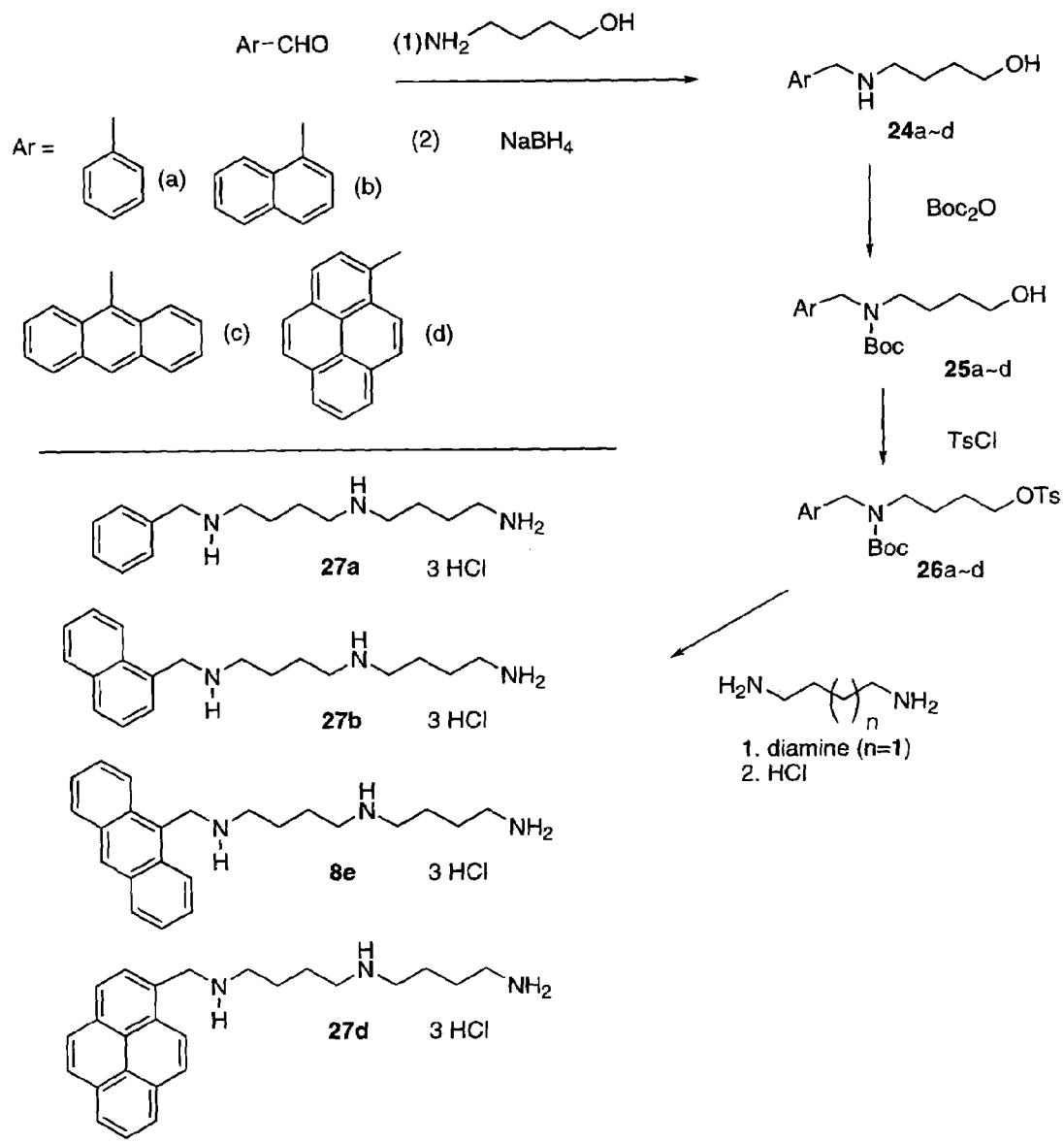
FIGS. 6A–6B (Schemes 6 and 7)—illustrates the synthesis of various aryl substituted polyamines (27a, 27b, 8e, 27d), a hydroxylated polyamine derivative 30 and a cyclohexyldiamine analogue 31.

As shown in FIG. 6A (Scheme 6), the aryl unit (Ar) was varied to include a variety of common arylalkyl units ($ArCH_2$). Using synthetic methods already described in Scheme 2, compounds 26a–d were reacted with diamines to form triamines 27a,b,d and 8e, which contain R=arylalkyl. Alternatively, they could be reacted with aminoalcohols, tosylated and reacted with diamines to form the tetraamine analogues similar to that outlined in FIG. 2C (Scheme 4) for the synthesis of 13.

Figure 6B:
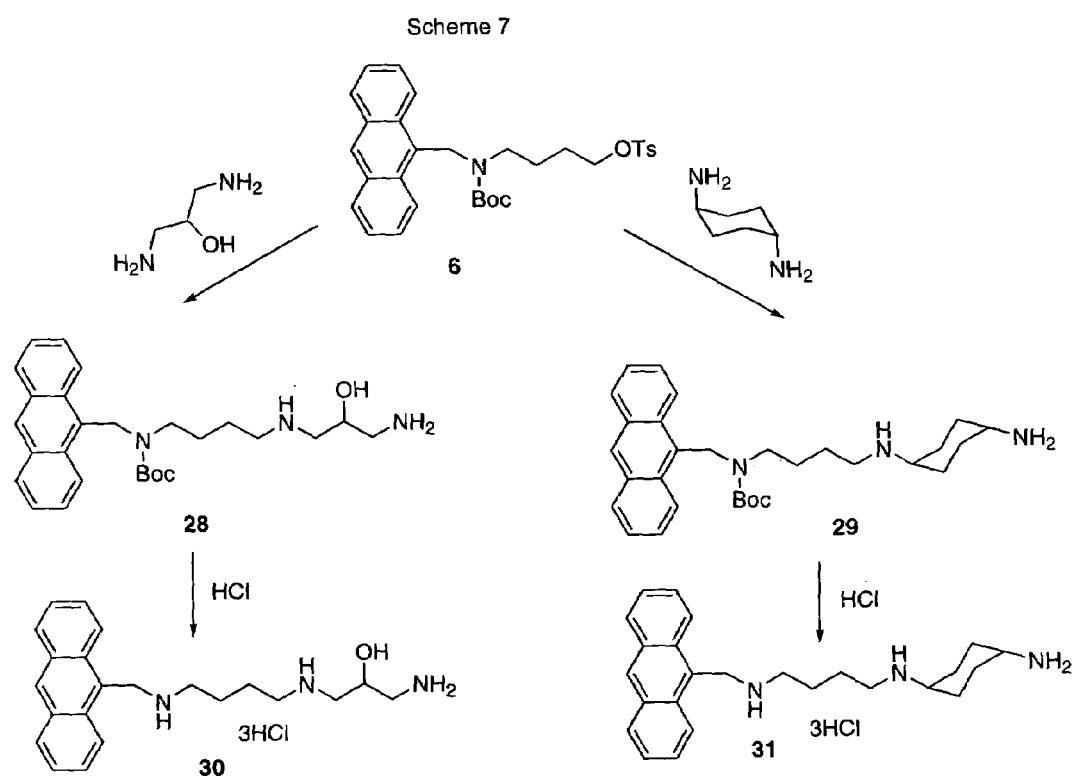

Internal modifications were also made to the aliphatic spacer unit connecting the nitrogens. For example as shown in FIG. 6B (Scheme 7), a hydroxy unit (30) or a cycloalkyl spacer unit (31) were inserted synthetically using a similar reaction of a diamine reacting with a tosylate (similar to how compounds 8 were made in Scheme 2).

Overall, the synthetic method is modular and allows for a variety of structural alterations to be introduced into the general architecture.

Biological Evaluation. Three cell lines were chosen for bioassay. L1210 (mouse leukemia) cells were selected for comparison with the published $IC_{50}$ and $K_i$ values determined for a variety of polyamine substrates. In this regard both $K_1$ and $IC_{50}$ values were measured in this line for comparison purposes. Chinese hamster ovary (CHO) cells were chosen along with a mutant cell line (CHO-MG) in order to comment on polyamine transporter affinity and cell selectivity. The CHO-MG cell line is polyamine-transport deficient and was isolated after chronic selection for growth resistance to methylglyoxalbis (guanylhydrazone). For the purposes of this study, the CHO-MG cell line represents cells with limited polyamine transport activity. In contrast, the parent CHO cell line illustrates cell types with active polyamine transport. Comparison of efficacy in these two lines provided an important screen to detect conjugate delivery via the polyamine transporter, PAT. For example, a conjugate with high utilization of the transporter would be very toxic to CHO cells, but less so to CHO-MG cells. Therefore, $IC_{50}$ determination in these two CHO lines provided a relative ranking of delivery via the PAT. In short, highly selective, vectored conjugates would give high (CHO-MG/CHO) $IC_{50}$ ratios.

It is a well-known practice in pharmaceutical science to use pharmaceutically acceptable acid salts of amine derivatives to facilitate their long storage and dosing as aqueous solutions. The examples listed in this invention are comprised of a polyamine salt derived from a pharmaceutically acceptable acid (e.g., HCl) with or without the use of a pharmaceutically acceptable carrier (e.g., water). Such salts can be derived from either inorganic or organic acids, including for example hydrochloric, hydrobromic, acetic, citric, fumaric, maleic, benzenesulfonic, and ascorbic acids. The pharmaceutical compositions obtained by the combination of the carrier and the polyamine salt will generally be used in a dosage necessary to elicit the desired biological effect. This includes its use in an antineoplastic effective amount or in a lesser amount when used in combination with other biologically active agents.

TABLE 1

Biological Evaluation of triamines 8b–g, N-tosyl derivatives 10a–d, tetraamines 13a–i, homologues 27, and controls 30–35 in L1210 cells.

| Compd (tether) | L1210 $IC_{50}$ in µM | L1210 + DFMO $IC_{50}$ in µM | L1210/ (L1210 + DFMO) $IC_{50}$ ratio | $K_i$ values (µM) L1210 cells |
|---|---|---|---|---|
| 8b (3,3) | 1.8 (±0.4) | 1.4 (±0.3) | 1.3 | 33.4 (±2.6) |
| 8c (3,4) | 0.7 (±0.3) | 0.3 (±0.1) | 2.3 | 2.5 (±0.3) |
| 8d (4,3) | 0.4 (±0.1) | 0.2 (±0.02) | 2 | 6.2 (±0.6) |
| 8e (4,4) | 0.3 (±0.04) | 0.15 (±0.1) | 2 | 1.8 (±0.1) |
| 8f (5,3) | 1.3 (±0.1) | 0.7 (±0.1) | 1.9 | 5.0 (±0.6) |
| 8g (5,4) | 0.4 (±0.1) | 0.3 (±0.1) | 1.3 | 1.7 (±0.2) |
| 10a (2,4) | 3.3 (±0.2) | 3.9 (±0.9) | 0.9 | ND |
| 10b (3,4) | 6.3 (±0.5) | 7.7 (±1.1) | 0.8 | ND |
| 10c (4,4) | 7.4 (±1.0) | 8.1 (±1.6) | 0.9 | ND |
| 10d (5,4) | 6.2 (±0.3) | 6.9 (±0.8) | 0.9 | ND |
| 13a (3,3,4) | 21.8 (±3.2) | 21.9 (±4.3) | 1 | 0.107 (±0.013) |
| 13b (3,4,3) | 19.5 (±2.8) | 31.9 (±1.9) | 0.6 | 0.202 (±0.008) |
| 13c (3,4,4) | 9.8 (±1.7) | 5.1 (±0.6) | 1.9 | 0.079 (±0.009) |
| 13d (3,5,4) | 10.7 (±2.4) | 7.2 (±0.1) | 1.5 | 0.090 (±0.006) |
| 13e (4,4,3) | 4.3 (±0.6) | 0.6 (±0.2) | 7.2 | 0.074 (±0.005) |
| 13f (4,4,4) | 7.5 (±0.3) | 1.6 (±0.3) | 4.7 | 0.051 (±0.006) |
| 13g (5,4,3) | 6.4 (±1.0) | 2.1 (±0.7) | 3 | 0.099 (±0.008) |
| 13h (5,4,4) | 7.2 (±0.6) | 3.8 (±0.1) | 1.9 | 0.065 (±0.005) |
| 13i (5,5,4) | 7.1 (±1.2) | 4.3 (±0.9) | 1.7 | 0.064 (±0.005) |
| 27a: benzyl (4,4) | 36.3 (±8.4) | 421 (±27.1) | 0.1 | 4.5 (±0.8) |
| 27b: naphthyl (4,4) | 0.50 (±0.03) | 0.43 (±0.02) | 1.1 | 3.8 (±0.5) |
| 27d: pyrenyl (4,4) | 0.40 (±0.02) | 0.36 (±0.06) | 1.1 | 2.9 (±0.3) |
| 30: Anthydroxyamino | 1.50 (±0.08) | 2.30 (±0.29) | 0.7 | 12.5 (±1.2) |
| 31: Ant(cyclohexyl) | 1.00 (±0.16) | 0.7 (±0.1) | 1.4 | 3.8 (±0.9) |
| 32: Ant(octylene) | 3.00 (±0.07) | 4.60 (±0.12) | 0.7 | 13.3 (±1.5) |
| 33: Ant(diethoxy) | 11.30 (±0.37) | 17.0 (±0.61) | 0.7 | 90.0 (±4.6) |
| 34: Antbutanediamine | 6.30 (±0.26) | 9.78 (±0.42) | 0.7 | 32.2 (±4.3) |
| 35: Ant(N-butyl) | 14.6 (±0.1) | 21.9 (±3.6) | 0.7 | 62.3 (±4.2) |

As shown in Table 1, L1210 cells which were pretreated with DFMO were more susceptible to the polyamine conjugates, which use the polyamine transporter (8b–8g). In contrast, DFMO pretreatment slightly reduced the potency of systems, which do not use the transporter (10a–10d). These conclusions were reached from the following two trends: a) the $IC_{50}$ values were lower for the triamine series (8b–8g) which use the transporter upon DFMO pretreatment and the $IC_{50}$ values were higher for the triamine series which have limited use of the transporter (10a–d) upon DFMO pretreatment. As expected, the tetraamine systems 13a–i were also effective in killing DFMO-pretreated cells. The homologous series 27b, 8e and 27d (in FIG. 6A, Scheme 6) revealed the structural tolerance of the polyamine transporter to import N-alkylaryl units of varying size and hydrophobicity. Research has shown that the compounds of the invention, mono-substituted $N^1$-alkylaryl triamines, have enhanced selectivity and cytotoxicity. The fact that 8e and cyclohexyl derivative 31 also had similar properties suggests that further alterations of the polyamine chain can be accommodated by the transporter. As expected, the control compounds 32–35 (FIG. 6) were all less cytotoxic than the vectored triamine systems, 8.

The $K_i$ values in Table 1 reflect the affinity of the polyamine derivative for the transport apparatus on the cell surface. The lower the $K_i$ value, the higher the affinity. Triamine-anthracene conjugates (which have a 4,4 triamine 8e and 5,4 triamine 8g sequence) were preferred and demonstrated the highest affinity for the polyamine transporter of the triamines tested. The tetraamines 13 had the lowest $K_i$ values and reflected their superior affinity for the polyamine transporter. However, their $IC_{50}$ values were typically higher than the corresponding triamine systems, which means they are less cytotoxic. This clearly illustrates that high affinity for the polyamine transporter does not always translate into higher cytotoxicity.

TABLE 2

Biological Evaluation of triamines 8b–g, N-tosyl derivatives 10a–d and tetraamines 13a–i, homologues 27, and controls 30–35, in the CHO and CHO-MG cell lines.

| Compd (tether) | CHO-MG $IC_{50}$ in $\mu M$ | CHO $IC_{50}$ in $\mu M$ | CHO-MG/CHO $IC_{50}$ ratio |
|---|---|---|---|
| 8b (3,3) | 3.4 (±0.5) | 1.9 (±0.4) | 1.8 |
| 8c (3,4) | 8.8 (±1.2) | 2.5 (±0.7) | 3.5 |
| 8d (4,3) | 9.5 (±1.1) | 0.4 (±0.1) | 24 |
| 8e (4,4) | 66.7 (±4.1) | 0.45 (±0.1) | 148 |
| 8f (5,3) | 10.1 (±1.2) | 4.1 (±0.5) | 2.5 |
| 8g (5,4) | 57.3 (±2.9) | 1.5 (±0.1) | 38 |
| 10a (2,4) | 7.1 (±0.4) | 5.1 (±0.6) | 1.4 |
| 10b (3,4) | 11.1 (±1.3) | 10.2 (±0.9) | 1.1 |
| 10c (4,4) | 10.6 (±1.9) | 10.4 (±1.6) | 1.0 |
| 10d (5,4) | 7.8 (±1.9) | 7.1 (±0.8) | 1.1 |
| 13a (3,3,4) | 41.5 (±3.5) | 44 (±0.0) | 0.9 |
| 13b (3,4,3) | 75.7 (±7.3) | 59.7 (±6.5) | 1.3 |
| 13c (3,4,4) | 52.8 (±2.6) | 31.2 (±7.3) | 1.7 |
| 13d (3,5,4) | 41.7 (±0.2) | 35 (±1.3) | 1.2 |
| 13e (4,4,3) | 2.8 (±0.4) | 4 (±1.4) | 0.7 |
| 13f (4,4,4) | 33.2 (±1.7) | 10.6 (±0.0) | 3.1 |
| 13g (5,4,3) | 33.5 (±3.5) | 18 (±3.5) | 1.9 |
| 13h (5,4,4) | 30.8 (±0.4) | 9.9 (±1.6) | 3.1 |
| 13i (5,5,4) | 5.7 (±1.6) | 4 (±0.8) | 1.4 |
| 27a:benzyl (4,4) | >1000 | >1000 | NA |
| 27c:naphthyl (4,4) | >100 | 0.6 (±0.2) | >164 |
| 27d:pyrenyl (4,4) | 15.5 (±2.4) | 0.46 (±0.05) | 34 |
| 30:Ant-(4,3-hydroxyamino) | 9.5 (±0.8) | 9.1 (±0.4) | 1 |
| 31:Ant-(cyclohexyl) | 17.4 (±2.8) | 2.5 (±0.5) | 7 |
| 32:Ant-(octylene) | 4.9 (±0.1) | 4.9 (±0.2) | 1 |
| 33:Ant-(diethoxy) | 15.9 (±1.5) | 12.6 (±0.6) | 1.3 |
| 34:Ant-diamine | 7.6 (±0.4) | 7.7 (±0.5) | 1 |
| 35:Ant (N-butyl) | 11.2 (±2.3) | 10.5 (±2.0) | 1.1 |

As shown in Table 2, biological evaluation of triamines 8b–g and 10a–d in CHO cells revealed that the 4,4-triamine 8e displays a nearly 150-fold preference for the CHO line containing PAT over CHO-MG, while the 3,3-triamine analogue 8b preferred this line by only 1.8 fold. Note: the entire tetraamine series 13 had, at best, only a 3 fold preference or lower. The naphthyl derivative 27b also had an excellent selectivity profile with >164 fold preference in killing cells with an active polyamine transport system. These findings demonstrate that triamine conjugates (particularly 8e and 27b, which both used the 4,4 triamine vector) make preferred cell targeting motifs. The effectiveness of the tri-amines is also reflected in the L1210 $IC_{50}$ results, wherein the 4,4-triamine 8e and 5,4-triamine 8g showed a greater sensitivity to DFMO treatment. Therefore, the triamine systems seem to give consistent data in all three cell lines.

Thus, the 4,4-triamine architecture represents a preferred vectoring system, which upon attachment to a toxic agent imparts high cell selectivity and low $IC_{50}$ values in the CHO and L1210 cell lines (Tables 1 and 2). In short, one can selectively deliver "large" toxic agents to tumor cells with highly active polyamine transporters by using the proper polyamine system for cell targeting.

An example of selectively targeting cancer cells (melanoma) with this strategy is illustrated in Table 3.

TABLE 3

Cell selectivity profile for 8e and the control N-butyl derivative 35.

| Cell Type | Time | Ant-4,4-triamine 8e $IC_{50}$ ($\mu M$) | Ant-N-butylamine 35 $IC_{50}$ ($\mu M$) |
|---|---|---|---|
| B16 (melanoma) | 24 h | 1.93 (±0.11) | 19.25 (±2.76) |
| B16 (melanoma) | 48 h | 1.10 (±0.07) | 21.31 (±2.18) |
| B16 (melanoma) | 72 h | 0.62 (±0.03) | 20.39 (±1.81) |
| Mel-A(normal melanocyte) | 24 h | 16.47 (±1.95) | 44.30 (±9.14) |
| Mel-A(normal melanocyte) | 48 h | 8.27 (±0.95) | 32.80 (±4.64) |
| Mel-A(normal melanocyte) | 72 h | 6.49 (±1.15) | 15.00 (±3.73) |

Figure 7:
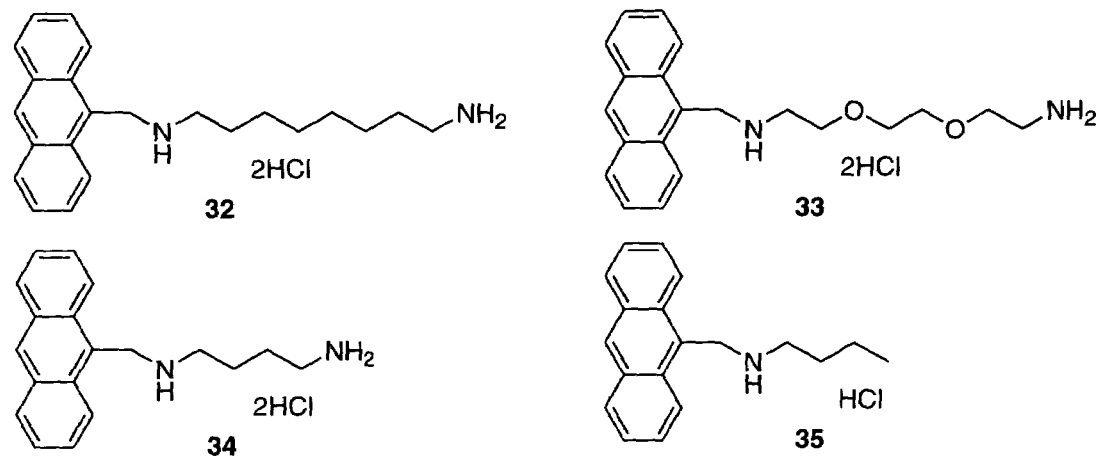
FIG. 7 illustrates the structures of 32–35 as examples of systems with altered amine scaffolds appended to an anthracenyl methyl unit.
Figure 8:
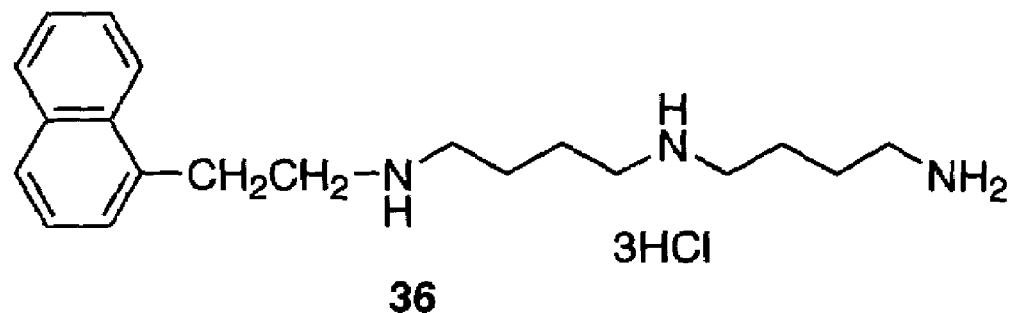
FIG. 8 illustrates a naphthylethyl triamine derivative, 36.
Figure 9:
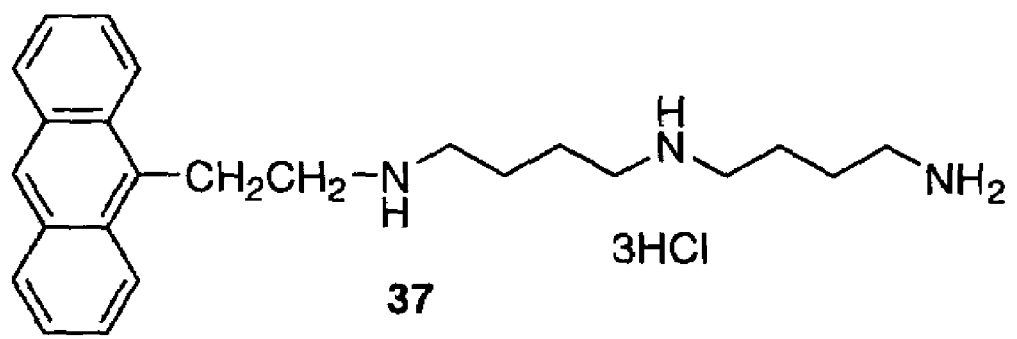
FIG. 9 illustrates an anthracenylethyl triamine derivative, 37.

Many cancer cell lines are known to have high PAT activity, and should be susceptible to this vectored chemotherapeutic strategy. As shown in Table 3, the triamine-vectored 8e analogue was 7.5–10.5 times more cytotoxic to melanoma B16 cells than the normal melanocytes, Mel-A (e.g. 6.49/0.62=10.5). The Ant-N-butyl control 35 (FIG. 7), which has been shown to not use the PAT, was only 0.7–2.3 fold more potent. Since the respective cell doubling times are different, $IC_{50}$ ratios (35/8e) for each cell type were also compared. This alternative interpretation revealed that the presence of the triamine vector in 8e resulted in 10–32 fold higher cytotoxicity in B-16 cells, which have high PAT activity, than control 35 (e.g., 24 h: 19.25/1.93=10). In contrast, the triamine vector in 8e resulted in only 2–4 fold higher cytotoxicity in Mel-A cells than 35 (e.g. 24 h: 44.3/16.47=2.7). These results further support the proposed polyamine vector strategy as a viable means to target cancer cells over their healthy counterparts.

With respect to the tetraamine systems, 13, the 4,4,4-tetraamine 13f and the 5,4,4-tetraamine 13h show enhanced selectivity in killing cells with active polyamine transporters (Table 2). The three-fold enhancement in cytotoxicity, while not as remarkable as the related triamine systems, distinguished these two tetraamines as the best of the tetraamine series studied.

Experimental Section

Materials. Silica gel (32–63 $\mu m$) was purchased from Scientific Adsorbents Incorporated. Chemical reagents were purchased either from the ACROS Chemical Co. or the Sigma Chemical Co. and used without further purification. All solvents were distilled prior to use. $^1H$ NMR and $^{13}C$ NMR spectra were recorded at 300 and 75 MHz, respectively. TLC solvent systems are based on volume % and $NH_4OH$ refers to concentrated aqueous $NH_4OH$. All final compounds listed in the Tables had satisfactory elemental analyses (a proof of purity).

General Procedure for the Synthesis of N-(Anthracen-9-ylmethyl)amino alcohols 4.

To a stirred solution of amino alcohol (12 mmol) in 25% MeOH/CH$_2$Cl$_2$ (10 mL) was added a solution of 9-anthraldehyde (10 mmol) in 25% MeOH/CH$_2$Cl$_2$ (10 mL) under N$_2$. The mixture was stirred at room temperature overnight until the imine formation was complete (monitored by TLC). The solvent was evaporated under vacuum to give the crude imine as a bright green solid, which was used for reduction without further purification.

NaBH$_4$ (30 mmol) was added in small portions to the solution of imine 1:1 CH$_3$OH:CH$_2$Cl$_2$ (20 mL) at 0° C. The mixture was stirred at room temperature overnight, then concentrated under vacuum. The residue was dissolved in CH$_2$Cl$_2$ (50 mL), and washed three times with aq. Na$_2$CO$_3$ (pH 10, 50 mL). The organic layer was separated, dried over anhydrous Na$_2$SO$_4$, filtered, and concentrated under vacuum. The residue was purified by flash chromatography on silica gel.

2-[(Anthracen-9-ylmethyl)-amino]ethanol, 4a. Bright yellow solid; mp 116–118° C.; yield 77%; R$_f$=0.48, methanol/chloroform, 1:9; $^1$H NMR (300 MHz, CDCl$_3$): δ 8.40 (s, 1H), 8.28 (d, 2H), 8.00 (d, 2H), 7.48 (m, 4H), 4.68 (s, 2H), 3.64 (t, 2H), 3.00 (t, 2H), 2.1 (br s, 2H); $^{13}$C NMR: δ 131.75, 131.44, 130.45, 129.47, 127.63, 126.48, 125.23, 124.18, 61.12, 51.65, 45.41; Anal. Calcd. for C$_{17}$H$_{17}$NO: C, 81.24; H, 6.82; N, 5.57; found: C, 81.28; H, 6.83; N, 5.57; HRMS (FAB) m/z calcd. for C$_{17}$H$_{18}$NO (M+H)$^+$: 252.1388; found: 252.1381.

3-[(Anthracen-9-ylmethyl)-amino]-propan-1-ol, 4b. Bright yellow solid; mp 82–83° C.; yield 80%; R$_f$=0.51, methanol/chloroform, 1:9; $^1$H NMR (300 MHz, CDCl$_3$): δ 8.40 (s, 1H), 8.28 (d, 2H), 8.00 (d, 2H), 7.46 (m, 4H), 4.70 (s, 2H), 3.80 (t, 2H), 3.10 (t, 2H), 2.90 (br s, 2H), 1.78 (m, 2H); $^{13}$C NMR: δ 131.72, 130.98, 130.48, 129.48, 127.72, 126.56, 125.25, 124.06, 64.65, 50.83, 46.02, 31.14. Anal. Calcd. for C$_{18}$H$_{19}$NO: C, 81.48; H, 7.22; N, 5.28. Found: C, 81.20; H, 7.20; N, 5.28. HRMS(FAB) m/z calcd. for C$_{18}$H$_{20}$NO(M+H)$^+$: 266.1545; found: 266.1526.

4-[(Anthracen-9-ylmethyl)-amino]-butan-1-ol, 4c. Bright yellow solid; mp 87–88° C.; yield 81%; R$_f$=0.51, methanol/chloroform, 1:9; $^1$H NMR (300 MHz, CDCl$_3$) δ 8.40 (s, 1H), 8.26 (d, 2H), 8.00 (d, 2H), 7.49 (m, 4H), 4.68 (s, 2H), 3.50 (t, 2H), 2.90 (t, 2H), 1.65 (br s, 4H); $^{13}$C NMR: δ 131.74, 130.73, 130.48, 129.51, 127.82, 126.64, 125.30, 123.96, 62.89, 50.58, 45.72, 32.72, 29.13. Anal. Calcd. for C$_{19}$H$_{21}$NO: C, 81.68; H, 7.58; N, 5.01. found: C, 81.63; H, 7.65; N, 5.10. HRMS (FAB) m/z calcd. for: C$_{19}$H$_{22}$NO (M+H)$^+$: 280.1701; found: 280.1679.

5-[(Anthracen-9-ylmethyl)-amino]-pentan-1-ol, 4d. Bright yellow solid; mp 76–77° C.; yield 68%; R$_f$=0.26, methanol/chloroform (5:95); $^1$H NMR (CDCl$_3$): δ 8.38 (s, 1H), 8.27 (d, 2H), 7.98 (d, 2H), 7.45 (m, 4H), 4.65 (s, 2H), 3.50 (t, 2H), 2.82(t, 2H), 1.78 (br s, 2H), 1.50 (m, 4H), 1.40 (m, 2H); $^{13}$C NMR (CDCl$_3$): δ 131.89, 131.77, 130.48, 129.44, 127.46, 126.40, 125.19, 124.29, 62.68, 50.60, 45.96, 32.68, 29.91, 23.67. Anal. Calcd. for C$_{20}$H$_{23}$NO: C, 81.87; H, 7.91; N, 4.77. found: C, 81.89; H, 7.99; N, 4.86. HRMS (FAB) m/z calcd. for C$_{20}$H$_{24}$NO (M+H)$^+$: 294.1858; found: 294.1835.

The General Procedure for the N-Boc protection of N-(Anthracen-9-ylmethyl)amino alcohols 4 to give 5. The solution of N-(anthracen-9-ylmethyl)-amino alcohol (5 mmol) in 20 mL of pyridine-methanol (1:5 v/v) was stirred at 0° C. for 10 min. A solution of di-tert-butyl dicarbonate (7.5 mmol) in methanol (5 mL) was added dropwise over ten minutes. The temperature was allowed to rise to room temperature and the reaction was stirred overnight. The mixture was evaporated to dryness under reduced pressure. The residue was dissolved in methylene chloride, and washed with deionized water several times. The organic layer was separated, dried over anhydrous Na$_2$SO$_4$, filtered, and concentrated under vacuum. The residue was purified by flash chromatography on silica gel.

Anthracen-9-ylmethyl-(2-hydroxy-ethyl) carbamic acid tert-butyl ester, 5a. Pale yellow solid; mp 131–132° C.; yield 84%; R$_f$=0.21 (acetone/hexane 1:4); $^1$H NMR (CDCl$_3$): δ 8.43 (s, 1H), 8.38 (br s, 2H), 8.01 (d, 2H), 7.43 (m, 4H), 5.50 (br s, 2H), 3.30 (t, 2H), 3.00 (br s, 3H, including —OH), 1.52 (br s, 9H). Anal. Calcd. for C$_{22}$H$_{25}$NO$_3$: C, 75.19; H, 7.17, N, 3.98. found. C, 75.02, H, 7.13, N, 3.98.

Anthracen-9-ylmethyl-(3-hydroxy-propyl) carbamic acid tert-butyl ester, 5b. Unstable pale yellow solid; yield 90%, R$_f$=0.23 (acetone/hexane 1:4); $^1$H NMR (CDCl$_3$): δ 8.42 (s, 1H), 8.36 (d, 2H), 8.02 (d, 2H), 7.52 (m, 4H), 5.50 (br s, 2H), 3.25 (br s, 2H), 3.10 (br s, 2H), 1.62 (m, 11H). HRMS (FAB): calcd. for C$_{23}$H$_{28}$NO$_3$ (M+H)$^+$: 366.2069; Found: 366.2067.

Anthracen-9-ylmethyl-(4-hydroxy-butyl) carbamic acid tert-butyl ester, 5c. Pale yellow solid; mp 113–114° C.; yield 88%; R$_f$=0.13(acetone/hexane 12:88); $^1$H NMR (CDCl$_3$): δ 8.42 (s, 1H), 8.39 (d, 2H), 8.01 (d, 2H), 7.52 (m, 4H), 5.50 (br s, 2H), 3.25 (t, 2H), 2.80 (br s, 2H), 1.60 (br s, 9H), 1.20 (m, 4H). $^3$C NMR: δ 155.88, 131.52, 131.48, 129.45, 128.99, 126.53, 125.22, 124.32, 80.08, 62.35, 44.54, 41.28, 30.05, 28.94 (3C), 24.99. Anal. Calcd. for C$_{24}$H$_{29}$NO$_3$: C, 75.96; H, 7.70; N, 3.69. found: C, 76.04; H, 7.64; N, 3.68. HRMS (FAB): calcd. for C$_{24}$H$_{29}$NO$_3$Na (M+Na)$^+$: 402.2045; found: 402.2070.

Anthracen-9-ylmethyl-(5-hydroxy-pentyl) carbamic acid tert-butyl ester, 5d. Pale yellow solid; mp 125–126° C.; yield 84%; R$_f$=0.28 (acetone/hexane 1:4); $^1$H NMR (CDCl$_3$): δ 8.44 (s, 1H), 8.41 (d, 2H), 8.05 (d, 2H), 7.55 (m, 4H), 5.56 (br s, 2H), 3.38 (t, 2H), 2.82 (br s, 2H), 1.64 (br s, 9H), 1.25 (m, 4H), 0.98 (m, 2H); $^{13}$C NMR: δ 155.97, 131.56, 131.53, 129.43, 128.34, 126.51, 125.23, 124.43, 79.94, 62.85, 44.84, 41.41, 32.33, 28.96(3C), 28.43, 23.14. Anal. Calcd. for C$_{25}$H$_{31}$NO$_3$: C, 76.30; H, 7.94; N, 3.56. found: C, 76.29; H, 7.96; N, 3.67. HRMS (FAB): calcd. for C$_{25}$H$_{32}$NO$_3$ (M+H)$^+$: 394.2382; found: 394.2385.

General Procedure for the tosylation of N-Boc protected (anthracen-9-ylmethyl)amino alcohols 4 to give 9. A solution of the N-Boc protected (anthracen-9-ylmethyl)amino alcohol (5 mmol) in 20 mL dry pyridine was stirred at 0° C. for 10 min. p-Toluenesulfonyl chloride (TsCl, 7.5 mmol) was added in small portions over 30 min. The mixture was stirred for an additional hour and the reaction flask was placed in a refrigerator (0–5° C.) overnight. The mixture was poured into 200 mL of ice-water, and a hemi-solid (or viscous liquid) typically precipitated (or separated). After decanting off the upper layer, the residue was dissolved in methylene chloride and washed several times with deionized water. The organic layer was separated, dried over anhydrous Na$_2$SO$_4$, filtered and concentrated under vacuum. The residue was purified by flash chromatography on silica gel.

Toluene-4-sulfonic acid 3-(anthracen-9-ylmethyl-tert-butoxycarbonyl-amino)-propyl ester, 9b. Unstable bright yellow viscous liquid, yield 51%; R$_f$=0.21 (acetone/hexane 1:4). $^1$H NMR (CDCl$_3$): δ 8.42 (s, 1H), 8.39 (d, 2H), 8.05 (d, 2H), 7.58 (m, 6H), 7.21 (d, 2H), 5.46 (s, 2H), 3.63 (t, 2H), 2.82 (t, 2H), 2.41 (s, 3H), 1.64 (br s, 11H). HRMS (FAB): calcd. for C$_{25}$H$_{26}$NO$_3$S (M+2H—Boc)$^+$: 420.1633; found: 420.1642.

Toluene-4-sulfonic acid 4-(anthracen-9-ylmethyl-tert-butoxycarbonyl-amino)-butyl ester, 9c. Pale yellow viscous liquid; yield 88%; $R_f$=0.38, acetone/hexane 1:3; $^1$H NMR (CDCl$_3$): δ 8.42 (s, 1H), 8.37 (d, 2H), 8.00 (d, 2H), 7.62 (d, 2H), 7.48 (m, 4H), 7.22 (d, 2H), 5.46 (s, 2H), 3.63 (t, 2H), 2.77 (br s, 2H), 2.40 (s, 3H), 1.48 (br s, 9H), 1.20 (br s, 4H); Anal. Calcd. for C$_{31}$H$_{35}$NO$_5$S 0.5H$_2$O: C, 68.61; H, 6.69; N, 2.58. found: C, 68.74; H, 6.57; N, 2.55. HRMS: calcd. for C$_{31}$H$_{35}$NO$_5$S M$^+$: 533.2236; found: 533.2236.

Toluene-4-sulfonic acid 5-(anthracen-9-ylmethyl-tert-butoxycarbonyl-amino)-pentyl ester, 9d. Pale yellow viscous liquid; yield 88%; $R_f$=0.25, acetone/hexane 1:4; $^1$H NMR (CDCl$_3$): δ 8.42 (s, 1H), 8.36 (d, 2H), 8.00 (d, 2H), 7.63 (d, 2H), 7.46 (m, 4H), 7.22 (d, 2H), 5.47 (s, 2H), 3.73 (br s, 2H), 2.76 (br s, 2H), 2.40 (s, 3H), 1.48 (br s, 9H), 1.24 (br s, 2H), 1.20 (br s, 2H), 0.93 (br s, 2H); Anal. Calcd. for C$_{32}$H$_{37}$NO$_5$S 0.5H$_2$O: C, 69.04; H, 6.88; N, 2.52. found: C, 69.15; H, 6.75; N, 2.57. HRMS (FAB): calcd. for C$_{32}$H$_{38}$NO$_5$S (M+H)$^+$: 548.2471; found: 548.2501.

General Procedure for the preparation of the N$^1$-Boc protected-N$^1$-(Anthracen-9-ylmethyl)-triamines, 7. The tosylated products 6 (1 mmol) and 1,4-diaminobutane or 1,3-diaminepropane (10 mmol) were dissolved in acetonitrile (10 mL), then stirred at 75° C. under N$_2$ overnight. After checking for the disappearance of the tosylate by TLC, the solution was concentrated under reduced pressure. The residue was dissolved in CH$_2$Cl$_2$ (20 mL) and washed three times with saturated aqueous sodium carbonate. The organic layer was separated, dried over anhydrous sodium sulfate, filtered, and concentrated under vacuum. The residue was purified by flash chromatography on silica gel. The purified products were used immediately for next step (BOC deprotection). The isolated yields ranged between 59–75%.

General Procedure for the preparation of the N$^1$— (Anthracen-9-ylmethyl)-triamines, 8. The N$^1$-Boc protected-N$^1$-(anthracen-9-ylmethyl)-triamine 7 (0.5 mmol) was dissolved in ethanol (5 mL), and stirred at 0° C. for 10 min. 4 N aq. HCl (8 mL) was added dropwise at 0° C. The mixture was stirred at room temperature overnight. The solution was then concentrated under reduced pressure (while maintaining the water bath on the rotary evaporator below 60° C.) and a bright yellow solid precipitated. The solids were washed several times with absolute ethanol and provided the pure target compounds. The $^1$H NMR spectra of polyamine conjugates were measured in 0.5 mL DMSO-d$_6$ and 3 drops of D$_2$O. The use of DMSO-d$_6$/D$_2$O mixtures resulted in better spectral resolution (compared to using pure D$_2$O as solvent). The $^{13}$C NMR spectra of the triamines were measured in D$_2$O to avoid the interference of DMSO carbon signals. The listed amines are all in their HCl salt form.

N-(3-Amino-propyl)-N-anthracen-9-ylmethyl-propane-1, 3-diamine, trihydrochloride 8b. Bright yellow solid, yield 98%. $^1$H NMR (DMSO-d$_6$+D$_2$O): δ 8.80 (s, 1H), 8.40 (d, 2H), 8.22 (d, 2H), 7.75 (t, 2H), 7.62 (t, 2H), 5.23 (s, 2H), 3.40 (t, 2H), 3.05 (m, 4H), 2.96 (t, 2H), 2.18 (m, 2H), 2.00 (m, 2H); $^{13}$C NMR: δ 130.63, 130.45, 130.06, 129.47, 127.72, 125.50, 122.48, 120.06, 44.91, 44.82, 44.75, 43.08, 36.74, 23.98, 22.93. Anal. Calcd. for C$_{21}$H$_{30}$Cl$_3$N$_3$: C, 58.54; H, 7.02; N, 9.75. found: C, 58.27; H, 6.90; N, 9.69. HRMS (FAB): calcd. for C$_{21}$H$_{30}$Cl$_2$N$_3$ (M+H—HCl)$^+$: 394.1817; found: 394.1806.

N$^1$-{3-[(Anthracen-9-ylmethyl)-amino]-propyl}-butane-1,4-diamine, trihydrochloride 8c. Bright yellow solid, yield 98%. $^1$H NMR (DMSO-d$_6$+D$_2$O): δ 8.80 (s, 1H), 8.42 (d, 2H), 8.20 (d, 2H), 7.72 (t, 2H), 7.62 (t, 2H), 5.23 (s, 2H), 3.42 (t, 2H), 3.05 (t, 2H), 2.98 (t, 2H), 2.82 (t, 2H), 2.20 (br s, 2H), 1.71 (br s, 4H). $^{13}$C NMR (D$_2$O): δ 130.57, 130.41, 130.01, 129.45, 127.71, 125.48, 122.46, 119.98, 47.27, 44.76, 44.66, 43.01, 39.03, 24.16, 23.00, 22.92. Anal. Calcd. for C$_{22}$H$_{32}$Cl$_3$N$_3$ 0.6H$_2$O: C, 57.99; H, 7.34; N, 9.22. found: C, 58.00; H, 7.36; N, 9.20. HRMS (FAB): calcd. for C$_{22}$H$_{32}$Cl$_2$N$_3$ (M+H—HCl)$^+$: 408.1973; found: 408.1950.

N-(3-Amino-propyl)-N-anthracen-9-ylmethyl-butane-1, 4-diamine, trihydrochloride 8d. Bright yellow solid, yield 95%. $^1$H NMR (DMSO-d$_6$+D$_2$O): δ 8.80(s, 1H), 8.42 (d, 2H), 8.20 (d, 2H), 7.73 (t, 2H), 7.64 (t, 2H), 5.23 (s, 2H), 3.30 (t, 2H), 2.99 (m, 6H), 2.00 (m, 2H), 1.80 (m, 4H). $^{13}$C NMR(D$_2$O): δ 130.65, 130.37, 130.04, 129.48, 127.70, 125.51, 122.49, 120.30, 47.18(2C), 44.78, 42.79, 36.81, 24.04, 23.14, 22.99. Anal. Calcd. for C$_{22}$H$_{32}$Cl$_3$N$_3$: C, 59.40; H, 7.25; N, 9.45. found: C, 59.48; H, 7.07; N, 9.30. HRMS (FAB): calcd. for C$_{22}$H$_{32}$Cl$_2$N$_3$ (M+H—HCl)$^+$: 408.1973; found: 408.1958.

N-(4-Amino-butyl)-N-anthracen-9-ylmethyl-butane-1,4-diamine, trihydrochloride 8e. Bright yellow solid, yield 91%. $^1$H NMR (DMSO-d$_6$+D$_2$O): δ 8.80 (s, 1H), 8.42 (d, 2H), 8.20 (d, 2H), 7.70 (t, 2H), 7.61 (t, 2H), 5.23 (s, 2H), 3.30 (t, 2H), 2.93 (m, 4H), 2.82 (t, 2H), 1.78–1.60 (m, 8H). $^{13}$C NMR (D$_2$O): δ 130.62, 130.32, 130.01, 129.45, 127.67, 125.48, 122.48, 120.37, 47.17, 47.11, 47.00, 42.76, 39.03, 24.19, 23.14, 23.02 (2C). Anal. Calcd. for C$_{23}$H$_{34}$Cl$_3$N$_3$ 0.8H$_2$O: C, 58.37; H, 7.58; N, 8.88. found: C, 58.39; H, 7.36; N, 8.76. HRMS (FAB): calcd. for C$_{23}$H$_{32}$N$_3$ (M+H-3HCl)$^+$: 350.2590; found: 350.2611.

N-(3-Amino-propyl)-N-anthracen-9-ylmethyl-pentane-1, 5-diamine, trihydrochloride 8f. Bright yellow solid, yield 86%. $^1$H NMR (DMSO-d$_6$+D$_2$O): δ 8.80 (s, 1H), 8.42 (d, H), 8.20 (d, 2H), 7.72 (t, 2H), 7.64 (t, 2H), 5.22 (s, 2H), 3.28 (t, 2H), 2.99 (m, 6H), 2.00 (m, 2H), 1.80 (m, 2H), 1.72 (m, 2H), 1.42 (m, 2H); $^{13}$C NMR (D$_2$O): δ 130.54, 130.23, 129.91, 129.39, 127.60, 125.42, 122.42, 120.30, 47.62, 47.54, 44.69, 42.56, 36.80, 25.28, 25.22, 24.01, 23.20. Anal. Calcd. for C$_{23}$H$_{34}$Cl$_3$N$_3$ 0.2H$_2$O: C, 59.73; H, 7.50; N, 9.09. found: C, 59.71; H, 7.40; N, 9.06. HRMS (FAB): calcd. for C$_{23}$H$_{34}$Cl$_2$N$_3$ (M+H—HCl)$^+$: 422.2130; found: 422.2106.

N-(4-Amino-butyl)-N-anthracen-9-ylmethyl-pentane-1, 5-diamine, trihydrochloride 8g. Bright yellow solid, yield 88%. $^1$H NMR (DMSO-d$_6$+D$_2$O): δ 8.80 (s, 1H), 8.42 (d, 2H), 8.20 (d, 2H), 7.73 (t, 2H), 7.64 (t, 2H), 5.23 (s, 2H), 3.26 (t, 2H), 2.93 (br s, 4H), 2.82(t, 2H), 2.00 (m, 2H), 1.80 (m, 2H), 1.72 (br s, 4H), 1.42 (m, 2H); $^{13}$C NMR (D$_2$O): δ 130.49, 130.21, 129.89, 129.38, 127.61, 125.41, 122.42, 120.23, 47.51, 47.46, 47.07, 42.50, 39.06, 25.29, 25.19, 24.22, 23.20, 23.04. Anal. Calcd. for C$_{24}$H$_{36}$Cl$_3$N$_3$: C, 60.95; H, 7.67; N, 8.89. found: C, 60.74; H, 7.63; N, 8.79. HRMS (FAB): calcd. for C$_{24}$H$_{36}$Cl$_2$N$_3$ (M+H—HCl)$^+$: 436.2286; found: 436.2289.

General Procedure for the Substitution of the Tosylated Compounds with the amino alcohols or diamines (Preparation of 11 or 13). The tosylated products (compounds 6 or 12) (1 mmol) and ωamino-α-alcohols (5 mmol) (or diamines when making 13) were dissolved in acetonitrile (10 mL), then stirred at 75° C. under N$_2$ overnight. After checking the diappearance of tosylated products by TLC, the solution was concentrated under reduced pressure. The residue was dissolved in CH$_2$Cl$_2$ (20 mL), washed three times with saturated aqueous sodium carbonate. The organic layer was separated, dried with anhydrous sodium sulfate, filtered, and concentrated under vacuum. The residue was purified by flash column on silica gel. The purified products 11 were used for next step immediately. During the synthesis of 13, an intermediate compound (13x), which still contained two N—BOC groups was isolated and immediately converted to 13 as described below.

General Procedure for the Amino Group Deprotection (Preparation of 13) The N—Boc protected $N^1$-(Anthracen-9-ylmethyl)-tetraamines (13x, 0.5 mmol) were dissolved in ethanol (5 mL), and stirred at 0° C. for 10 min. 4N HCl (8 mL) then added dropwise at 0° C. The mixture was stirred at room temperature overnight. After that the solution was concentrated under reduced pressure below 60° C., and the bright yellow solid precipitated. The solid was washed with 100% ethanol for several times and to give the pure target compounds 13.

$N^1$-{3-[3-(Anthracen-9-ylmethyl)-amino]-propylamino}-butane-1,4-diamine Tetrahydrochloride (13a) Bright yellow solid; yield 96%; $^1$H NMR: δ 8.72 (s, 1H), 8.28 (d, 2H), 8.16 (d, 2H), 7.64 (t, 2H), 7.58 (t, 2H), 5.20 (br s, 2H), 3.38 (br s, 2H), 3.00(m, 8H), 2.84 (br s, 2H), 2.12 (br s, 2H), 2.00 (br s, 2H), 1.62(br s, 4H). $^{13}$CNMR: δ130.73, 130.54, 130.17, 129.55, 127.82, 125.59, 122.57, 120.17, 47.38, 44.91(2C), 44.83, 44.70, 43.19, 39.11, 24.25, 23.09, 22.99(2C). Anal. Calcd. for $C_{25}H_{40}Cl_4N_4H_2O$: C, 53.96; H, 7.61; N, 10.07. found: C, 53.89; H, 7.62; N, 10.08. HRMS(FAB): calcd. for $C_{25}H_{37}N_4$ (M+H-4HCl)$^+$: 393.3013; found: 393.3020

N-(3-Amino-propyl)-N-{3-[(anthracen-9-ylmethyl)-amino]-propyl}-butane-1,4-diamine Tetrahydrochloride (13b) Bright yellow solid; yield 91%; $^1$H NMR: δ 8.73 (s, 1H), 8.28 (d, 2H), 8.17 (d, 2H), 7.64 (t, 2H), 7.58 (t, 2H), 5.18 (s, 2H), 3.30 (t, 2H), 2.96(m, 10H), 2.10 (m, 2H), 1.90 (m, 2H), 1.60(br s, 4H). $^{13}$CNMR: δ130.70, 130.51, 130.13, 129.51, 127.77, 125.55, 122.54, 120.15, 47.25(2C), 44.81 (2C), 44.71, 43.12, 36.81, 24.06, 23.05(2C), 22.97. Anal. Calcd. for $C_{25}H_{40}Cl_4N_4$ 0.4H$_2$O: C, 55.03; H, 7.54; N, 10.27. found: C, 55.02; H, 7.49; N, 10.18. HRMS (FAB): calcd. for $C_{25}H_{37}N_4$ (M+H-4HCl)$^+$: 393.3013; found: 393.3018

N-(4-Amino-butyl)-N-{3-[(anthracen-9-ylmethyl)-amino]-propyl}-butane-1,4-diamine Tetrahydrochloride (13c) Bright yellow solid; yield 95%; $^1$H NMR: δ 8.80 (s, 1H), 8.40 (d, 2H), 8.19 (d, 2H), 7.66 (t, 2H), 7.60 (t, 2H), 5.21 (s, 2H), 3.40 (t, 2H), 3.02(t, 2H), 2.92(m, 6H), 2.82(t, 2H), 2.11 (m, 2H), 1.62(m, 8H). $^{13}$CNMR: δ130.85, 130.62, 130.29, 129.57, 127.86, 125.64, 122.61, 120.38, 47.26, 47.18, 47.10, 44.86, 44.72, 43.25, 39.06, 24.23, 23.07(2C), 22.99. Anal. Calcd. for $C_{26}H_{42}Cl_4N_4$ 1.2H$_2$O: C, 54.40; H, 7.80; N, 9.76. found: C, 54.43; H, 7.67; N, 9.79. HRMS (FAB): calcd. for $C_{26}H_{39}N_4$ (M+H-4HCl)$^+$: 407.3175; found: 407.3165

N-(4-Amino-butyl)-N-{3-[(anthracen-9-ylmethyl)-amino]-propyl}-pentane-1,5-diamine Tetrahydrochloride (13d) Bright yellow solid; yield 88%; $^1$H NMR: δ 8.70 (s, 1H), 8.28 (d, 2H), 8.15 (d, 2H), 7.63 (t, 2H), 7.58 (t, 2H), 5.20 (s, 2H), 3.38 (t, 2H), 3.01(t, 2H), 2.90(m, 8H), 2.11 (m, 2H), 1.62(br s, 8H), 1.28(m, 2H). $^{13}$CNMR: δ130.71, 130.52, 130.14, 129.53, 127.80, 125.57, 122.55, 120.16, 47.70, 47.54, 47.12, 44.84, 44.65, 43.13, 39.10, 25.39(2C), 24.26, 23.16, 23.08, 22.97. Anal. Calcd. for $C_{27}H_{44}Cl_4N_4$ 1.0H$_2$O: C, 55.48; H, 7.93; N, 9.59. found: C, 55.52; H, 7.97; N, 9.56. HRMS (FAB): calcd. for $C_{27}H_{41}N_4$ (M+H-4HCl)$^+$: 421.3326; found: 421.3327

N-[4-(3-Amino-propylamino)-butyl]-N-anthracen-9-ylmethyl-butane-1,4-diamine Tetrahydrochloride (13e) Bright yellow solid; yield 94%; $^1$H NMR: δ 8.79 (s, 1H), 0.40 (d, 2H), 8.19 (d, 2H), 7.68 (t, 2H), 7.60 (t, 2H), 5.21 (s, 2H), 3.28 (t, 2H), 2.92(m, 10H), 1.92 (m, 2H), 1.80(m, 2H), 1.70(br s, 6H). $^{13}$CNMR: δ130.69, 130.41, 130.09, 29.49, 127.73, 125.53, 122.52, 120.37, 47.28, 47.20, 47.12, 47.06, 44.81, 42.82, 36.82, 4.05, 23.15, 23.08(2C), 23.01. Anal. Calcd for $C_{26}H_{42}Cl_4N_4$ 0.5H$_2$O: C, 55.62; H, 7.72; N, 9.98. found: C, 55.62; H, 7.55; N, 9.85. HRMS (FAB): calcd. for $C_{26}H_{39}N_4$ (M+H-4HCl)$^+$: 407.3169; found: 407.3166

N-[4-(4-Amino-butylamino)-butyl]-N-anthracen-9-ylmethyl-butane-1,4-diamine Tetrahydrochloride (13f) Bright yellow solid; yield 86%; $^1$HNMR: δ8.79 (s, 1H), 8.40 (d, 2H), 8.19 (d, 2H), 7.68 (t, 2H), 7.60 (t, 2H), 5.21 (s, 2H), 3.24 (br s, 2H), 2.92(br s, 8H), 2.84(br s, 2H), 1.80 (br s, 2H), 1.64(br s, 10H). $^{13}$CNMR: δ130.75, 130.46, 130.14, 129.53, 127.77, 125.57, 122.57, 120.45, 47.24, 47.20, 47.14 (2C), 47.08, 42.88, 39.09, 24.26, 23.18, 23.12(2C), 23.10, 23.06. Anal. Calcd. for $C_{27}H_{44}Cl_4N_4$ 0.2H$_2$O: C, 56.89; H, 7.85; N, 9.83. found: C, 56.82; H, 7.87; N, 9.76. HRMS (FAB): calcd. for $C_{27}H_{41}N_4$ (M+H-4HCl)$^+$: 421.3326; found: 421.3310

N-[4-(3-Amino-propylamino)-butyl]-N-anthracen-9-ylmethyl-pentane-1,5-diamine Tetrahydrochloride (13g) Bright yellow solid; yield 88%; $^1$HNMR: δ8.79 (s, 1H), 8.40 (d, 2H), 8.19 (d, 2H), 7.66 (t, 2H), 7.60 (t, 2H), 5.20 (s, 2H), 3.22 (t, 2H), 2.90(m, 10H), 1.92 (m, 2H), 1.66(m, 8H), 1.40(m, 2H). $^{13}$CNMR: δ130.70, 130.36, 130.07, 129.49, 127.72, 125.54, 122.53, 120.50, 47.64, 47.53, 47.30, 47.05, 44.82, 42.69, 36.84, 25.36, 25.28, 24.07, 23.27, 23.11, 23.09. Anal. Calcd. for $C_{27}H_{44}Cl_4N_4$ 0.5H$_2$O: C, 56.35; H, 7.88; N, 9.74. found: C, 56.36; H, 7.76; N, 9.77. HRMS (FAB): calcd. for $C_{27}H_{41}N_4$ (M+H-4HCl)$^+$: 421.3326; found: 421.3319

N-[4-(4-Amino-butylamino)-butyl]-N-anthracen-9-ylmethyl-pentane-1,5-diamine Tetrahydrochloride (13h) Bright yellow solid; yield 92%; $^1$HNMR: δ8.78 (s, 1H,), 8.39 (d, 2H), 8.18 (d, 2H), 7.66 (t, 2H), 7.60 (t, 2H), 5.20 (s, 2H), 3.22 (t, 2H), 2.88(br s, 8H), 2.80(m, 2H), 1.74 (m, 2H), 1.62(br s, 10H), 1.40(m, 2H). $^{13}$CNMR: δ130.70, 130.36, 130.07, 129.49, 127.72, 125.54, 122.53, 120.50, 47.64, 47.53, 47.20, 47.14, 47.06, 42.70, 39.08, 25.36, 25.28, 24.24, 23.27, 23.12(2C), 23.08. Anal. Calcd. for $C_{28}H_{46}Cl_4N_4$ 0.6H$_2$O: C, 56.88; H, 8.05; N, 9.48. found: C, 56.89; H, 7.92; N, 9.40. HRMS(FAB): calcd. for $C_{28}H_{43}N_4$ (M+H-4HCl)$^+$: 435.3482; found: 435.3477.

N-[5-(4-Amino-butylamino)-pentyl]-N-anthracen-9-ylmethyl-pentane-1,5-diamine Tetrahydrochloride (13i) Bright yellow solid; yield 99%; $^1$H NMR: δ8.70 (s, 1H), 8.28 (d, 2H), 8.13 (d, 2H), 7.66 (t, 2H), 7.56 (t, 2H), 5.24 (s, 2H), 3.16 (t, 2H), 2.88(m, 10H), 1.70 (m, 2H), 1.58(m, 10H), 1.32(m, 4H). $^{13}$C NMR: δ130.69, 130.35, 130.06, 129.49, 127.70, 125.52, 122.52, 120.50, 47.62, 47.56, 47.48, 47.44, 47.11, 42.67, 39.08, 25.42(2C), 25.34, 25.27, 24.25, 23.27, 23.21, 23.07. Anal. Calcd. for $C_{29}H_{48}Cl_4N_4$ 0.7H$_2$O: C, 57.37; H, 8.20; N, 9.23. found: C, 57.27; H, 8.11; N, 9.14. HRMS (FAB): calcd. for $C_{29}H_{45}N_4$ (M+H-4HCl)$^+$: 449.3644; found: 449.3650.

Synthesis of 23. A mixture of doxorubicin 21 (1 equiv.) and {4-[tert-butoxycarbonyl-(4-oxo-butyl)-amino]-butyl}-carbamic acid tert-butyl ester 20 (2 equiv.) in 25% methanol-dichloromethane (5 mL) were stirred at 0° C. for several minutes, then added 1M NaBH$_3$CN in THF (0.67 equiv.) (FIG. 5). After checking the disappearance of doxorubicin by TLC and a new less polar spot formed, the solution was concentrated and the residue was purified by preparative TLC. R$_f$=0.38 (10% methanol-chloroform) to give 23. Compound 23: $^1$H NMR (CDCl$_3$) δ 8.05 (d, 1H, H1), 7.80 (t, 1H, H2), 7.41 (d, 1H, H3), 5.52 (m, 1H, H1'), 5.33 (m, 1H, H7), 4.77 (m, 2H, H14), 4.58 (m, 1H, NHCO), 4.10 (s, 3H, OCH$_3$), 3.98 (q, 1H, H5'), 3.61 (m, 1H, H4'), 3.29 (d, 1H, H10), 3.22–3.02 (m, 7H, 1H, H4', 3xCH$_2$), 2.79 (m, 1H, H3'), 2.59 (m, 2H, NCH$_2$), 2.40 (d, 1H, H8), 2.16 (dd, 1H, H8), 1.75 (m, 1H, H2'), 1.70–1.35 (m, 30H, H2', 8xCH$_2$, 6xCH$_3$).

4-(N-Benzylamino)-butan-1-ol (24a). Pale yellow liquid; yield 89%; $R_f$=0.34, methanol/chloroform, 1:4); $^1$H NMR (300 MHz, CDCl$_3$) δ 7.29 (brs, 5H), 3.77 (s, 2H), 3.59 (t, 2H), 2.68 (t, 2H), 1.65 (brs, 4H); $^{13}$C NMR: δ138.8, 128.4 (2C), 128.1 (2C), 127.1, 62.5, 53.7, 49.1, 32.4, 28.5; HRMS (FAB) m/z calcd. for C$_{11}$H$_{18}$NO(M+H)$^+$: 180.1388; found: 180.1389.

N-(Naphthalen-1-ylmethyl)-4-amino-butan-1-ol (24b). Dark yellow liquid; yield 93.6%; $R_f$=0.54, methanol/chloroform, 1:4); $^1$H NMR (300 MHz, CDCl$_3$) δ 8.02 (d, 1H), 7.85 (d, 1H), 7.76 (d, 1H), 7.47 (m, 4H), 4.23 (s, 2H), 3.58 (t, 2H), 2.79 (t, 2H), 2.51 (brs, 2H), 1.68 (brs, 4H); $^{13}$C NMR: δ 134.5, 133.6, 131.3, 128.6, 127.8, 126.2, 126.1, 125.5, 125.2, 122.9, 62.4, 51.0, 49.6, 32.1, 28.3; HRMS m/z calcd. for C$_{15}$H$_{19}$NO(M$^+$): 229.1467; found: 229.1477.

4-[(Anthracen-9-ylmethyl)-amino]-butan-1-ol (24c). See 4c above.

4-[(Pyren-1-ylmethyl)-amino]-butan-1-ol (24d). White solid; yield 94%. $^1$H NMR (300 MHz, CDCl$_3$): δ 8.24 (d, 2H), 8.13 (m, 4H), 7.96 (m, 4H), 4.42 (s, 2H), 3.56 (t, 2H), 2.82 (t, 2H), 1.64 (brs, 4H). $^{13}$C NMR (CDCl$_3$): 132.4, 131.0, 130.6, 130.5, 128.7, 127.7, 127.2, 127.0 (2C), 125.7, 125.0, 124.9, 124.8, 124.6 (2C), 122.4, 62.6, 51.3, 49.6, 32.3, 28.6. HRMS (FAB): calcd. for C$_{21}$H$_{22}$NO(M+H)$^+$: 304.1701; found: 304.1701.N-(4-Amino-butyl)-N'-benzene-1-ylmethyl-butane-1,4-diamine Trihydrochloride (27a). White solid; yield 73%. $^1$H NMR (300 MHz, DMSO+D$_2$O): δ 7.47 (br s, 2H), 7.41 (br s, 3H), 4.09 (s, 2H), 2.88 (br s, 6H), 2.78 (br s, 2H), 1.63 (br s, 8H). $^{13}$C NMR (D$_2$O): 130.7, 129.9 (2C), 129.8, 129.4 (2C), 51.3, 47.13, 47.07, 46.5, 39.0, 24.2, 23.1, 23.0 (2C); HRMS (FAB): calcd. for C$_{15}$H$_{28}$N$_3$ (M+H-3HCl)$^+$: 250.2283; found: 250.2268.

N-(4-Amino-butyl)-N'-naphthalen-1-ylmethyl-butane-1,4-diamine Trihydrochloride (27b). White solid; yield 80%. $^1$H NMR (300 MHz, D$_2$O): δ 8.03 (br s, 1H), 7.96 (br s, 2H), 7.59 (br s, 2H), 7.53 (br s, 1H), 7.51 (br s, 1H), 4.68 (s, 2H), 3.14 (t, 2H), 2.99 (m, 6H), 1.67 (br s, 8). $^{13}$C NMR (D$_2$O): 132.9, 130.2, 129.9, 128.8, 128.5, 126.8, 126.0, 125.8, 125.0, 121.9, 47.4, 46.5, 46.4, 46.3, 38.4, 23.5, 22.5, 22.4 (2C); HRMS(FAB): calcd. for C$_{19}$H$_{30}$N$_3$ (M+H-3HCl)$^+$: 300.2440; found: 300.2431.

N-(4-Amino-butyl)-N'-pyren-1-ylmethyl-butane-1,4-diamine Trihydrochloride (27d). White solid; yield 94%. $^1$H NMR (300 MHz, D$_2$O): δ 8.1~7.6 (m, 9H), 4.46 (s, 2H), 3.04 (m, 2H), 2.92 (m, 6H), 1.63 (br s, 8H). $^{13}$C NMR (D$_2$O): δ 131.3, 130.4, 129.7, 128.4, 128.2, 127.9, 126.9, 126.3, 125.7, 125.6, 124.53, 124.51, 123.1, 122.9, 122.5, 120.9, 47.9, 47.0, 46.9, 46.6, 39.0, 24.1, 23.0, 22.9 (2C). HRMS (FAB): calcd. for C$_{25}$H$_{31}$N$_3$(M+H-3HCl)$^+$: 374.2596; found: 374.2594.

1-Amino-3-{4-[(anthracen-9-ylmethyl)-amino]-butylamino}-propan-2-ol Trihydrochloride (30) Bright yellow solid, yield 95%. $^1$H NMR (DMSO-d$_6$+D$_2$O): δ 8.80 (s, 1H), 8.42 (d, 2H), 8.20 (d, 2H), 7.68 (t, 2H), 7.60 (t, 2H), 5.22 (s, 2H), 4.20(m, 1H), 3.28 (t, 2H), 3.1~2.80 (m, 6H), 1.78 (brs, 4H). $^{13}$C NMR (D$_2$O): δ 130.6, 130.4, 130.0, 129.5, 127.7, 125.5, 122.5, 120.3, 63.8, 50.1, 47.3, 47.2, 42.8, 42.4, 23.0, 22.9. HRMS (FAB): calcd. for C$_{22}$H$_{30}$N$_3$O (M+H-3HCl)$^+$: 352.2389; found: 352.2381.

N-{4-[(Anthracen-9-ylmethyl)-amino]-butyl}-cyclohexane-1,4-diamine Trihydrochloride (31). Bright yellow solid, yield 95%. $^1$H NMR (CD$_3$OD): δ 8.68 (s, 1H), 8.41 (d, 2H), 8.17 (d, 2H), 7.68 (t, 2H), 7.57 (t, 2H), 5.34 (s, 2H), 3.40 (m, 2H), 3.16 (m, 4H), 2.26(m, 2H), 2.20(m, 2H), 1.90(m, 4H), 1.60(m, 4H); $^{13}$C NMR(D$_2$O): δ 130.7, 130.4, 130.1, 129.5, 127.7, 125.5, 122.5, 120.3, 55.4, 48.7, 47.1, 44.3, 42.8, 28.2, 26.8, 23.3, 23.0. HRMS (FAB): calcd. for C$_{25}$H$_{34}$N$_3$ (M+H-3HCl)$^+$: 376.2753; found: 376.2747.

N$^1$-Anthracen-9-ylmethyl-octane-1,8-diamine Dihydrochloride (32). yellow solid; yield 89%; $^1$H NMR (300 MHz, CD$_3$OD) δ 8.69 (s, 1H), 8.40 (d, 2H), 8.15 (d, 2H), 7.70 (t, 2H), 7.59 (t, 2H), 5.32 (s, 2H), 3.30 (br s, 2H), 2.92 (t 2H), 1.82 (m, 2H), 1.63 (m, 2H), 1.42 (br s, 8H); $^{13}$C NMR (D$_2$O): δ 130.6, 130.3, 130.0, 129.4, 127.6, 125.5, 122.4, 120.5, 47.8, 42.3, 39.7, 28.2, 28.1, 26.9, 25.9, 25.7, 25.4; HRMS (FAB) m/z calcd. for C$_{23}$H$_{31}$N$_2$ (M+H-2HCl)$^+$: 335.2487; found: 335.2489.

2-(2-{2-[(Anthracen-9-ylmethyl)-amino]-ethoxy}-ethoxy)-ethylamine Dihydrochloride (33). Bright yellow solid; yield 81%; $^1$H NMR (300 MHz, DMSO-d$_6$+D$_2$O) δ 8.80 (s, 1H), 8.40 (d, 2H), 8.20 (d, 2H), 7.68 (t, 2H), 7.60 (t, 2H), 5.24 (s, 2H), 3.82 (t, 2H), 3.66 (m, 4H), 3.60 (t, 2H), 3.40 (t, 2H), 2.96 (t, 2H); $^{13}$C NMR(D$_2$O): δ 130.8, 130.5, 130.1, 129.5, 127.7, 125.6, 122.5, 120.5, 69.8 (2C), 66.6, 65.1, 47.0, 42.5, 39.2. HRMS (FAB) m/z calcd. for: C$_{21}$H$_{27}$N$_2$O$_2$ (M+H-2HCl)$^+$: 339.2073; found: 339.2074.

N$^1$-Anthracen-9-ylmethyl-butane-1,4-diamine Dihydrochloride (34). Yellow solid; yield 21%; $R_f$=0.11, methanol/chloroform, 1:20+3 drops of NH$_4$OH); $^1$H NMR (300 MHz, D$_2$O): δ 8.55 (br s, 1H), 8.15 (d, 2H), 8.08 (d, 2H), 7.66 (m, 4H), 5.08 (br s, 2H), 3.25 (t, 2H), 3.0 (t, 2H), 1.76 (m, 4H); $^{13}$C NMR (D$_2$O): δ 130.6, 130.3, 129.9, 129.4, 127.6, 125.4, 122.4, 120.2, 47.2, 42.7, 38.6, 24.2, 22.9; ESI-MS m/z calcd. for C$_{19}$H$_{23}$N$_2$ (M+H): 279.2; found: 279.2.

N$^1$-Anthracen-9-ylmethyl-butylamine Monohydrochloride (35) Compound 35 was synthesized in 58% yield by reductive amination of anthraldehyde and butylamine followed by treatment with 4N aq. HCl. 35: Yellow solid; yield 58%; $R_f$=0.5, methanol/chloroform, 1:20+1 drop of NH$_4$OH; $^1$H NMR (300 MHz, DMSO-d$_6$): δ9.1 (br s, 2H, NH$_2$ salt), 8.78 (s, 1H), 8.51 (d, 2H), 8.18 (d, 2H), 7.64 (m, 4H), 5.2 (br s, 2H), 3.2 (s, 2H), 1.73 (t, 2H), 1.36 (q, 2H), 0.92 (q, 3H); $^{13}$C NMR (CDCl$_3$): δ 131.6, 131.26, 130.55, 129.46, 128.05, 125.72, 123.89, 120.86, 46.05, 41.92, 28.48, 20.32, 13.79. Anal. Calcd for C$_{15}$H$_{22}$NCl,0.2H$_2$O: C, 75.21; H, 7.44; N, 4.62; found: C, 75.31; H, 7.44; N, 4.56.

As is apparent from the above Tables 1–3, a limited class of N-alkylarylpolyamine compounds (i.e. N-naphthylalkyl, N-anthracenylalkyl and N-pyrenylalkyl) have unique properties of surprising cytotoxicity, unexpected selectivity in killing cancer cells (especially cells with high polyamine transport activity), and/or facilitate the delivery of known toxic agents into cancer cells. As shown in Table 2, the N-(3-Amino-propyl)-N-anthracen-9-ylmethyl-butane-1,4-diamine, trihydrochloride (8d), N-(4-Amino-butyl)-N-anthracen-9-ylmethyl-butane-1,4-diamine, trihydrochloride (8e), N-(4-Amino-butyl)-N-anthracen-9-ylmethyl-pentane-1,5-diamine, trihydrochloride (8g), N-(4-Amino-butyl)-N'-naphthalen-1-ylmethyl-butane-1,4-diamine trihydrochloride (27b), N-(4-Amino-butyl)-N'-pyren-1-ylmethyl-butane-1,4-diamine trihydrochloride (27d), and N-{4-[(Anthracen-9-ylmethyl)-amino]-butyl}-cyclohexane-1,4-diamine trihydrochloride (31) have outstanding selectivity in targeting and killing cells with active polyamine transporters.

N-Alkylpolyamines can be broken down into their dealkylated components by cellular metabolic pathways. For example, a N-alkyl-4,4-triamine (RNH(CH$_2$)$_4$NH(CH$_2$)$_4$NH$_2$, where R is alkyl) can be converted into homospermidine, H$_2$N(CH$_2$)$_4$NH(CH$_2$)$_4$NH$_2$. It has been found that the N-alkylaryl group has an influence on this breakdown pathway. Surprisingly, cells treated with compound 8e did not form homospermidine, which indicated stability towards this form of degradation.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

I claim:

1. A compound of formula A,

A:

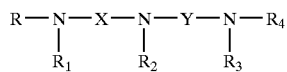

or a pharmaceutically acceptable salt thereof, wherein R is selected from the group consisting of naphthylmethyl, naphthylethyl, anthracenylmethyl, anthracenylethyl, $R^1$, $R^2$, $R^3$, $R^4$ are selected from at least one of hydrogen, alkyl, cycloalkyl, alkylaryl, where X is at least one of cycloalkyl and $(CH_2)_r$, and r is 2–18, where Y is at least one of cycloalkyl and $(CH_2)_s$ and s is 2–18.

2. The compound according to claim 1, wherein R is selected from the group consisting of naphthylmethyl, naphthyethyl, antracenylmethyl, antracenylethyl, $R^1$, $R^2$, $R^3$, and $R^4$ are hydrogen and r and s are 2–5 or a pharmaceutically acceptable salt thereof.

3. The compound according to claim 1, which is N-(3-Amino-propyl)-N-anthracen-9-ylmethyl-butane-1,4-diamine, trihydrochloride or a pharmaceutically acceptable salt thereof.

4. The compound according to claim 1, which is N-(4-Amino-butyl)-N-anthracen-9-ylmethyl-butane-1,4-diamine, trihydrochloride or a pharmaceutically acceptable salt thereof.

5. The compound according to claim 1, which is N-(4-Amino-butyl)-N-anthracen-9-ylmethyl-pentane-1,5-diamine, trihydrochloride or a pharmaceutically acceptable salt thereof.

6. The compound according to claim 1, which is, N-(4-Amino-butyl)-N'-naphthalen-1-ylmethyl-butane-1,4-diamine, trihydrochloride or a pharmaceutically acceptable salt thereof.

7. The compound according to claim 1, which is N-{4-[(Anthracen-9-ylmethyl)-amino]-butyl}-cyclohexane-1,4-diamine, trihydrochloride or a pharmaceutically acceptable salt thereof.

8. A compound of the formula B,

B: 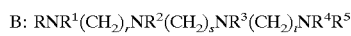

or a pharmaceutically acceptable salt thereof, wherein R is selected from the group consisting of naphthylmethyl, naphthylethyl, anthracenylmethyl, anthracenylethyl, pyrenylmethyl, wherein $R^1$, $R^2$, $R^3$, $R^4$, and $R^5$ are selected from at least one of the following: hydrogen, alkyl, cycloalkyl, alkylaryl, r is 2–18, s is 2–18 and t is 2–18.

9. The compound according to claim 8, wherein $R^1$, $R^2$, $R^3$, $R^4$, and $R^5$ are hydrogen or a pharmaceutically acceptable salt thereof.

10. The compound according to claim 9, wherein r, s and t are 2–5.

11. The compound according to claim 8, which is N-[4-(4-Amino-butylamino)-butyl]-N-anthracen-9-ylmethyl-butane-1,4-diamine, tetrahydrochloride or a pharmaceutically acceptable salt thereof.

12. The compound according to claim 8, which is N-[4-(4-Amino-butylamino)-butyl]-N-anthracen-9-ylmethyl-pentane-1,5-diamine, tetrahydrochloride or a pharmaceutically acceptable salt thereof.

13. The pharmaceutical composition comprising an antineoplastic effective amount of a polyamine according to claim 1 and a pharmaceutically acceptable carrier thereof.

14. The pharmaceutical composition comprising an antineoplastic effective amount of a polyamine according to claim 8 and a pharmaceutically acceptable carrier thereof.

15. The compound according to claim 1 that is useful in vectoring systems that attach to anti-cancer drugs to improve chemotherapeutic potency without involving the immune system.

16. A compound of formula A,

A:

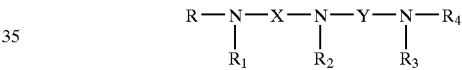

or a pharmaceutically acceptable salt thereof, wherein R is selected from the group consisting of naphthylmethyl, naphthylethyl, anthracenylmethyl, anthracenylethyl, pyrenylmethyl, $R^1$, $R^2$, $R^3$, $R^4$ are selected from at least one of hydrogen, alkyl, cycloalkyl, alkylaryl, where X is at least one of cycloalkyl and $(CH_2)_r$, and r is 2–18, where Y is at least one of cycloalkyl and $(CH_2)_s$ and s is 2–18 that is useful in vectoring systems that attach to anti-cancer drugs to improve chemotherapeutic potency.

17. The compound according to claim 16, which is N-(4-Amino-butyl)-N'-pyren-1-ylmethyl-butane-1,4-diamine, trihydrochloride or a pharmaceutically acceptable salt thereof.

* * * * *